United States Patent
Susin et al.

(10) Patent No.: US 10,759,843 B2
(45) Date of Patent: Sep. 1, 2020

(54) METHOD AND PHARMACEUTICAL COMPOSITION FOR USE IN THE TREATMENT OF CANCER

(71) Applicants: Santos Susin, Paris (FR); Pierre Launay, Paris (FR); Philippe Karoyan, Paris (FR); Helene Merle-Beral, Paris (FR)

(72) Inventors: Santos Susin, Paris (FR); Pierre Launay, Paris (FR); Philippe Karoyan, Paris (FR); Helene Merle-Beral, Paris (FR)

(73) Assignee: Philippe Karoyan, Paris (FR)

( * ) Notice: Subject to any disclaimer, the term of this patent is extended or adjusted under 35 U.S.C. 154(b) by 0 days.

(21) Appl. No.: 16/161,931

(22) Filed: Oct. 16, 2018

(65) Prior Publication Data

US 2019/0135898 A1    May 9, 2019

Related U.S. Application Data

(63) Continuation of application No. 15/687,692, filed on Aug. 28, 2017, now abandoned, which is a continuation of application No. 14/874,657, filed on Oct. 5, 2015, now abandoned, which is a continuation of application No. 14/406,091, filed as application No. PCT/EP2013/061727 on Jun. 6, 2013, now Pat. No. 9,198,949.

(30) Foreign Application Priority Data

Jun. 6, 2012 (EP) .................................. 12305636

(51) Int. Cl.
| | | |
|---|---|---|
| A61K 38/00 | (2006.01) | |
| C07K 14/78 | (2006.01) | |
| C07K 7/06 | (2006.01) | |
| A61K 38/08 | (2019.01) | |
| A61K 48/00 | (2006.01) | |

(52) U.S. Cl.
CPC .............. *C07K 14/78* (2013.01); *A61K 38/08* (2013.01); *C07K 7/06* (2013.01); *A61K 38/00* (2013.01); *A61K 48/00* (2013.01)

(58) Field of Classification Search
None
See application file for complete search history.

(56) References Cited

U.S. PATENT DOCUMENTS

| | | | |
|---|---|---|---|
| 5,595,756 A * | 1/1997 | Bally .................. | A61K 9/1272 264/4.1 |
| 5,610,271 A | 3/1997 | Dooley et al. | |
| 5,827,498 A | 10/1998 | Seki et al. | |
| 6,355,451 B1 | 3/2002 | Lees et al. | |
| 7,223,731 B2 | 5/2007 | Lawler | |
| 2006/0188508 A1 * | 8/2006 | Cohen .................. | C07K 14/4747 424/155.1 |

FOREIGN PATENT DOCUMENTS

| | | |
|---|---|---|
| JP | 2009013142 A | 1/2009 |
| JP | 2009201379 A | 9/2009 |

OTHER PUBLICATIONS

Mateo, et al., "CD47 Ligation Induces Caspase-independent Cell Death in Chronic Lymphocytic Leukemia", Nature Medicine, Nov. 1, 1999, vol. 5, No. 11, p. 1277-1284 (Year: 1999).*
Bruel, A., et al Thrombospondin-1 TSP-1 and Tsp-1 derived heparin-binding peptides induce promyelocytic leukemia cell differentiation and apoptosis, Anticancer Research, vol. 251 Mar. 2005, pp. 757-764 (Year: 2005).*
Veliz & Pinilla-Ibarz, Treatment of Relapsed or Refractory Chronic Lymphocytic Leukemia, Cancer Control, Jan. 2012, vol. 19, No. 1, pp. 37-53 (Year: 2012).*
John C. Byrd, "The mechanism of tumor cell clearance by rituximab in vivo in patients with B-cell chronic lymphocytic leukemia: evidence of caspase activation and apotosis induction," Blood, 2002, vol. 99, No. 3, 1038-1043 (7 pages total) (Year: 2002).*
Sporn et at, "Chemoprevention of Cancer," Carcinogenesis, vol. 21 (2000), 525-530 (Year: 2000).*
Gura, "Cancer Models: Systems for Identifying New Drugs Are Often Faulty," Science vol. 278 (1997), 1041-1042 (Year: 1997).*
Kanda et al, Role of Thrombospondin-1-Derived Peptide, 4N1K, in FGF-2-Induced Angiogenesis Experimental Cell Research 252, 262-272 (1999) (Year: 1999).*
Mateo V et al., "CD47 ligation induces caspase-independent cell death in chronic lymphocytic leukemia", Nature Medicine, Nature Publishing Group, New York, NY, US, (Nov. 1, 1999), vol. 5, No. 11, doi:10.1038/15233, ISSN 1078-8956, pp. 1277-1284.
Partha Manna et al., "CD47 mediates killing of breast tumor cells via Gi-dependent inhibition of protein kinase A.", Cancer Research, (Feb. 1, 2004), vol. 64, No. 3, ISSN 0008-5472, pp. 1026-1036.
Bruel et al., "Thrombospondin-1 (TSP-1) and TSP-1-deprived heparin-binding peptides induce promyelocylic leukemia cell differentiation and apoptosis", Anticancer Research, vol. 25, (Mar. 1, 2005), pp. 757-764.
Yasuyoshi Miyata et al., "Expression of thrombospondin-derived 4N1K peptide-containing proteins in renal cell carcinoma tissues is associated with a decrease in tumor growth and angiogenesis.", Clinical Cancer Research, (May 1, 2003), vol. 9, pp. 1734-1740.

(Continued)

*Primary Examiner* — Thomas S Heard
(74) *Attorney, Agent, or Firm* — Arent Fox LLP

(57) ABSTRACT

The present invention relates to a soluble peptide comprising the amino acids sequence: KRFYVVMWKK (SEQ ID NO:1) or a function-conservative variant thereof for use in the treatment of cancer.
The invention also relates to a pharmaceutical composition for use in the treatment of cancer comprising at least one soluble peptide according to the invention or at least one acid nucleic according to the invention or at least one expression vector according to the invention, or at least one host cell according to the invention and a pharmaceutically acceptable carrier.

9 Claims, 9 Drawing Sheets

Figure 1:
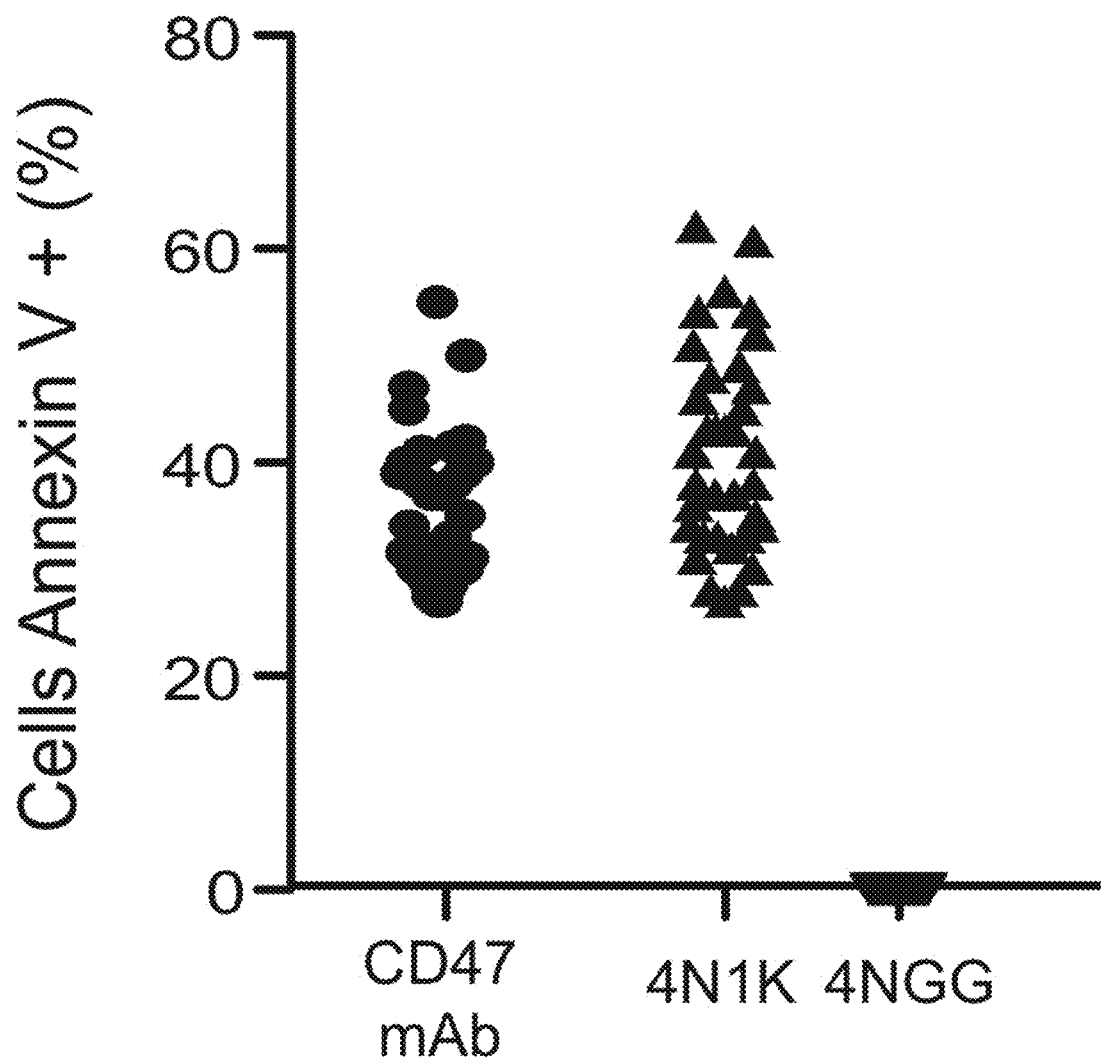

Specification includes a Sequence Listing.

(56) References Cited

OTHER PUBLICATIONS

Barbier et al., "Caspase-independent type III programmed cell death in chronic lymphocytic leukemia: the key role of the F-actin cytoskeleton", Haematologica, (Apr. 1, 2009), vol. 94, No. 4, doi:10.3324/haematol.13690, ISSN 0390-6078, pp. 507-517.
Sporn et al., "Chemoprevention of Cancer", Carcinogenesis, vol. 21 (2000), 525-530.
Gura. "Cancer Models: Systems for Identifying New Drugs Are Often Faulty", Science vol. 278 (1997), 1041-1042.
Amino Acids, Dec. 1, 2016 pp. 1-3.
Hammen PK et al., "The loss in hydrophobic surface area resulting from a Leu to Val mutation at the N-terminus of the aldehyde dehydrogenase presequence prevents import of the protein into mitochondria.", Protein SCI., (1999) Apr. 8(4):890-6.
FDA announces first U.S. gene therapy approval, (2017), pp. 1-3.
Seth P. "Vector-mediated cancer gene therapy: an overview." Cancer Biol Ther. (May 2005), 4(5):512-7.
Veliz M. & Pinilla-Ibarz J. "Treatment of relapsed or refractory chronic lymphocytic leukemia." Cancer Control. (Jan. 2012), 19(1):37-53.
Tugyi R. et al., "Partial D-amino acid substitution: Improved enzymatic stability and preserved Ab recognition of a MUC2 epitope peptide." Proc Natl Acad Sci USA. (Jan. 11, 2005), 102(2):413-8.

\* cited by examiner

A
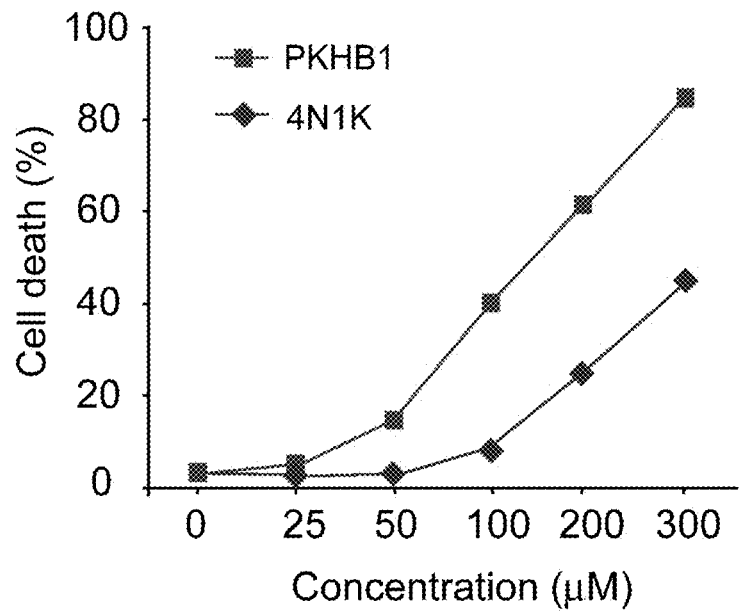
B
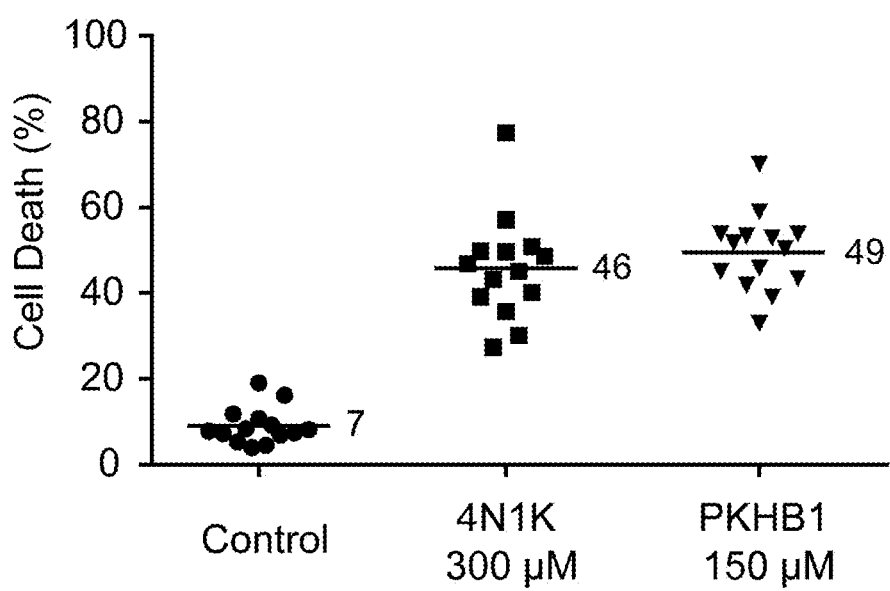
Figure 6 A and B

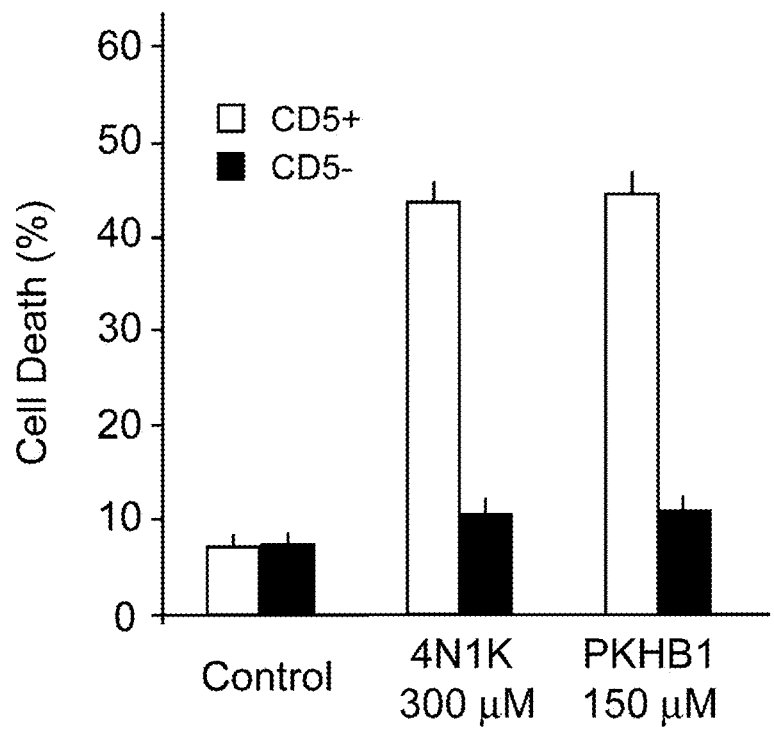
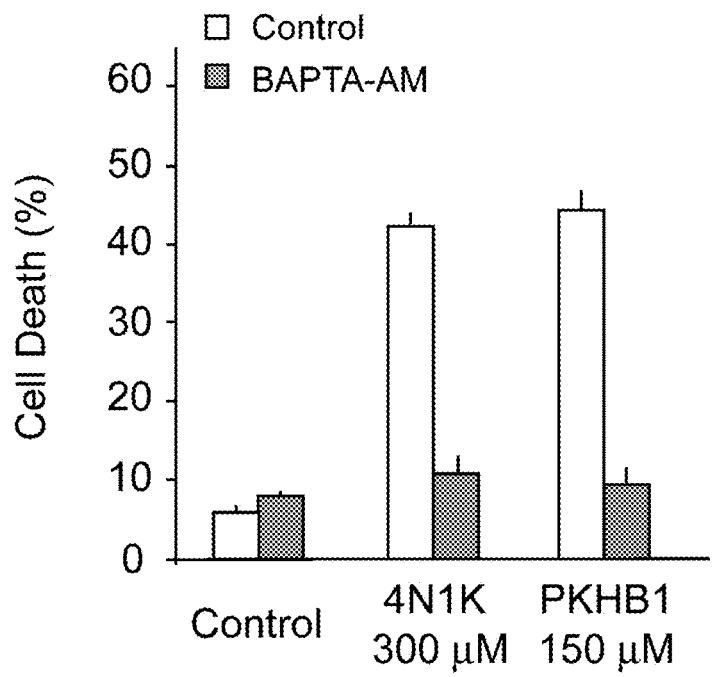
Figure 6 C and D

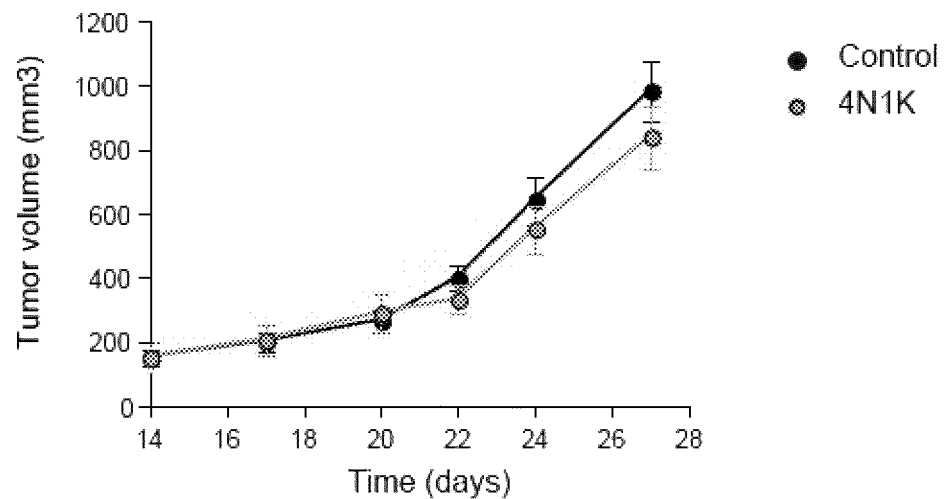
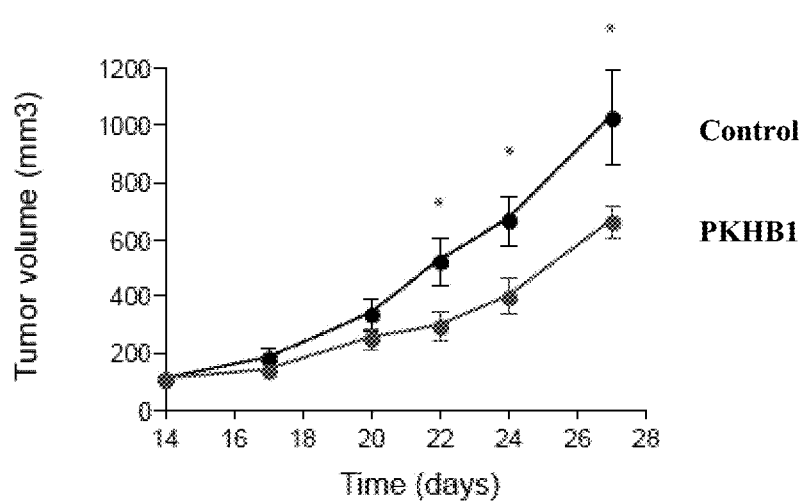
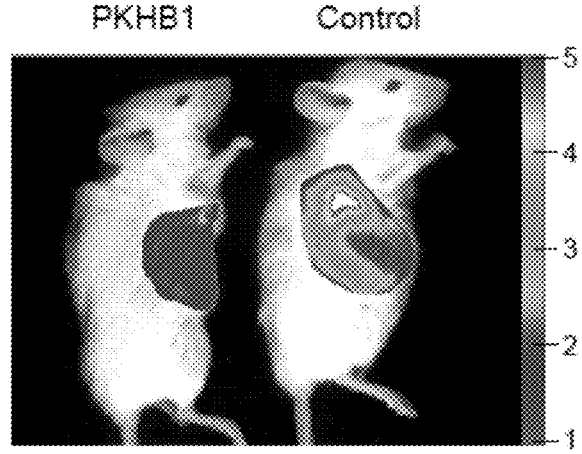
Figure 7 A, B and C

SEQUENCE LISTING

```
<160> NUMBER OF SEQ ID NOS: 5

<210> SEQ ID NO 1
<211> LENGTH: 10
<212> TYPE: PRT
<213> ORGANISM: Artificial
<220> FEATURE:
<223> OTHER INFORMATION: Synthetic peptide

<400> SEQUENCE: 1

Lys Arg Phe Tyr Val Val Met Trp Lys Lys
1               5                   10

<210> SEQ ID NO 2
<211> LENGTH: 10
<212> TYPE: PRT
<213> ORGANISM: Artificial
<220> FEATURE:
<223> OTHER INFORMATION: Synthetic Peptide

<400> SEQUENCE: 2

Lys Arg Phe Tyr Gly Gly Met Trp Lys Lys
1               5                   10

<210> SEQ ID NO 3
<211> LENGTH: 8
<212> TYPE: PRT
<213> ORGANISM: Artificial
<220> FEATURE:
<223> OTHER INFORMATION: Synthetic peptide

<400> SEQUENCE: 3

Arg Phe Tyr Val Val Met Trp Lys
1               5

<210> SEQ ID NO 4
<211> LENGTH: 8
<212> TYPE: PRT
<213> ORGANISM: Artificial
<220> FEATURE:
<223> OTHER INFORMATION: Synthetic peptide

<400> SEQUENCE: 4

Lys Trp Met Val Val Tyr Phe Arg
1               5

<210> SEQ ID NO 5
<211> LENGTH: 10
<212> TYPE: PRT
<213> ORGANISM: Artificial
<220> FEATURE:
<223> OTHER INFORMATION: Synthetic peptide
```

```
<400> SEQUENCE: 5

Lys Lys Trp Met Val Val Tyr Phe Arg Lys
1               5                   10
```

METHOD AND PHARMACEUTICAL COMPOSITION FOR USE IN THE TREATMENT OF CANCER

CROSS REFERENCE TO RELATED APPLICATIONS

This application is a continuation of U.S. application Ser. No. 15/687,692 filed Aug. 28, 2017, which is a continuation of U.S. application Ser. No. 14/874,657 filed Oct. 5, 2015, which is a continuation of U.S. application Ser. No. 14/406,091, now U.S. Pat. No. 9,198,949 issued on Dec. 1, 2015, which is a 35 U.S.C. 371 National Phase of PCT Application No. PCT/EP2013/061727 filed Jun. 6, 2013, which claims priority to EP Patent Application No. 12305636.8 filed Jun. 6, 2012, the disclosures of each of which is incorporated herein by reference.

FIELD OF THE INVENTION

The present invention relates to a soluble peptide comprising the amino acids sequence: KRFYVVMWKK (SEQ ID NO:1) or a function-conservative variant thereof for use in the treatment of cancer.

The invention also relates to a pharmaceutical composition for use in the treatment of cancer comprising at least one soluble peptide according to the invention or at least one acid nucleic according to the invention or at least one expression vector according to the invention, or at least one host cell according to the invention and a pharmaceutically acceptable carrier.

BACKGROUND OF THE INVENTION

Cancer is a malignant neoplasm, is a broad group of various diseases, all involving unregulated cell growth. In 2007, cancer caused about 13% of all human deaths worldwide (7.9 million). Rates are rising as more people live to an old age and as mass lifestyle changes occur in the developing world.

Particularly, Chronic Lymphocytic Leukemia (CLL) is the most common adult leukemia in the Western countries and is characterized by a progressive accumulation of monoclonal $CD5^+$ B-lymphocytes in the peripheral blood, bone marrow, and secondary lymphoid organs. The resulting congestion leads to the progressive failure of the immune and hematopoietic systems. High-risk hallmarks predictive of CLL progression include the cytogenetic features' mutation/deletion of 17p13 (TP53) and 11q22-q23 (ATM), IGHV unmutated status, high expression of ZAP70, CD38, soluble CD23 increase and the currently studied and not still validated mutations in NOTCH1, MYD88, BIRC3, XPO1, KLHL6, SF3B1, and POT1 genes [Gribben J G, 2010; Lanasa M C, 2010 and Chiorazzi N. et al., 2005]. Patients with dysfunction relevant to ATM and TP53 genes have the poorest prognosis requiring specific aggressive therapy including allogenic stem cell transplantation [Pospisilova N, 2012]. The characteristics of CLL are: (i) Incurable, as all patients will eventually relapse, underscoring a resistance of the disease to current treatment options. (ii) Very heterogeneous disease in terms of response to the—yet non-optimal—existing treatments. (iii) Drug resistance remains a major cause of treatment failure in CLL and its inevitable fate due to the prolonged natural course of the disease and the repeated treatments, creating a relevant social and health problem. (iv) Mainly affects elderly people and is considered a paradigmatic example of most age-related cancers. (v) Robust and specific markers predictive of response to treatment are still lacking, though urgently needed in order to implement risk-adapted, personalized treatment and maximize clinical benefit while minimizing costs.

Even though the direct cause for the development of this malignancy is not fully understood, it is now well demonstrated that CLL represents a perfect example of a human malignancy caused by an imbalance between proliferation and Programmed Cell Death (PCD) [Chiorazzi N, 2007]. Thus, a better understanding of PCD mechanisms regulating the lifespan of the leukemic CLL cells should provide key advances for therapeutic interventions in this leukemia.

PCD is a self-destruction process characterized by stereotyped ultrastructural changes including mitochondrial alterations, condensation of the nucleus and cytoplasm, membrane blebbing and external display of phosphatidylserine. Intense research performed in the last decade has identified a multitude of enzymes and other regulatory proteins involved in the modulation of PCD. These studies conclude that, in most cases, PCD occurs when a family of cysteine proteases, known as caspases, is activated. Since the induction of apoptosis through the use of caspase activators may theoretically constitute a treatment for cancer, the initial pro-apoptotic anti-cancer trials have focused on caspase activity. Unfortunately, most of these studies are still in preclinical development because of their low efficacy. In part, this may be due to the fact that PCD can proceed even when the caspase cascade is blocked. This fact has revealed the existence of an alternative pathway defined as caspase-independent. A comprehensive analysis of caspase-independent PCD pathways offers therefore a new challenge in the design of therapeutic strategies against CLL and other neoplastic diseases.

As indicated above, drug resistance remains a major cause of treatment failure in CLL. In fact, current therapies are responsible for several side effects, increasing the occurrence of treatment-related disabilities that may ultimately affect the well-being, if not the survival rate, of most patients. Until now, the goal of therapy has been to maintain the best quality of life and start treatment only when patients became symptomatic from their disease. For the majority of patients this means following a "wait-and-see" approach to determine the rate of progression of the disease and assess the development of symptoms. Initial treatments for CLL patients have included either a nucleosid analog (Fludarabine) or an alkylating agent (Chlorambucil). This initial approach has been improved by combination regimens such as fludarabine and cyclophosphamide (FC), or more recently by the addition of rituximab to FC (FCR treatment) that is now accepted as the standard front-line therapy. Alternative treatments have been developed for resistant patients or in relapse such as bendamustine, proteasome inhibitors, or monoclonal antibodies (anti-CD52, optimized anti-CD20, anti-CD23, etc.).

Concerning the current clinical trials, the more relevant are the use of monoclonal antibodies (GA101, lumiliximab, lucatumumab), BH3 mimetics (obatoclax, ABT-263), cyclin-dependent kinase inhibitors (flavopiridol, SNS-032), Lyn-kinase inhibitors (dasatinib, bafetinib), hypomethylating agents (azacytidine, decitabine), histone deacetylase inhibitors (parobinastat), purine analogs (8-chloroadenosine, forodesine), and small modular immunopharmaceuticals (TRU-016). Molecules inhibiting downstream signaling after B-cell receptor ligation are novel oral agents interacting at different targets including phosphatidylinositol 3-kinase inhibitors (CAL-101), Bruton's tyrosine kinase (BTK) (PCI-32765), and Spleen Tyrosine Kinase (SYK)-inhibitors (fostamitinib).

Most of the above-described chemotherapeutic treatments induce cytotoxicity via a caspase-dependent mechanism (see above, page 2) with a quite variable outcome, with many patients having a positive reaction whereas others remain refractory (15-25% of CLL patients become refractory during the course of the disease). Indeed, as leukemic B cells present molecular defects that make them particularly resistant to the caspase-dependent PCD pathway (p53 inactivation, overexpression of anti-apoptotic proteins, such as Mcl-1 or Bcl-2), a significant group of CLL patients are refractory to the current chemotherapeutic treatments. For that reason, the introduction of new drugs that induce PCD via alternative caspase-independent PCD pathways could provide new means of improving the current therapeutic strategies used in CLL treatment.

The CD47 receptor is a widely expressed member of the immunoglobulin (Ig) superfamily, functioning both as a receptor for thrombospondin-1 (TSP-1) and as a ligand for the transmembrane signal regulatory proteins SIRPα and γ [Brown E J et al., 2001]. These molecules regulate various biological phenomena in the immune system, including platelet activation, leukocyte migration, macrophage multinucleation, and PCD. Neither SIRPα nor SIRPγ has been implicated in CD47-induced PCD in contrast to TSP-1, which has been shown to bind CD47 specifically via its COOH-terminal cell-binding domain. Many cancers appear to upregulate CD47 as a mechanism of immune evasion and recent work showed that CD47 is a prognostic factor and a potential therapeutic target in different types of Non-Hodgkin Lymphomas (NHL), including CLL [Edris, B et al., 2012; Willingham, S. B et al., 2012; Chao, M. P et al., 2010; Jaiswal, S et al., 2009 and Chao, M. P et al., 2011]. The inventors and others have recently demonstrated that CD47 ligation, by an immobilized anti-CD47 mAb (not by a soluble anti-CD47), induces caspase-independent PCD, even in CLL cells from refractory patients [Mateo V et al., 1999; Roue G et al., 2003; Barbier S et al., 2009; Merle-Beral H et al., 2009; Bras M et al., 2007; Mateo V et al., 2002].

SUMMARY OF THE INVENTION

Figure 8:
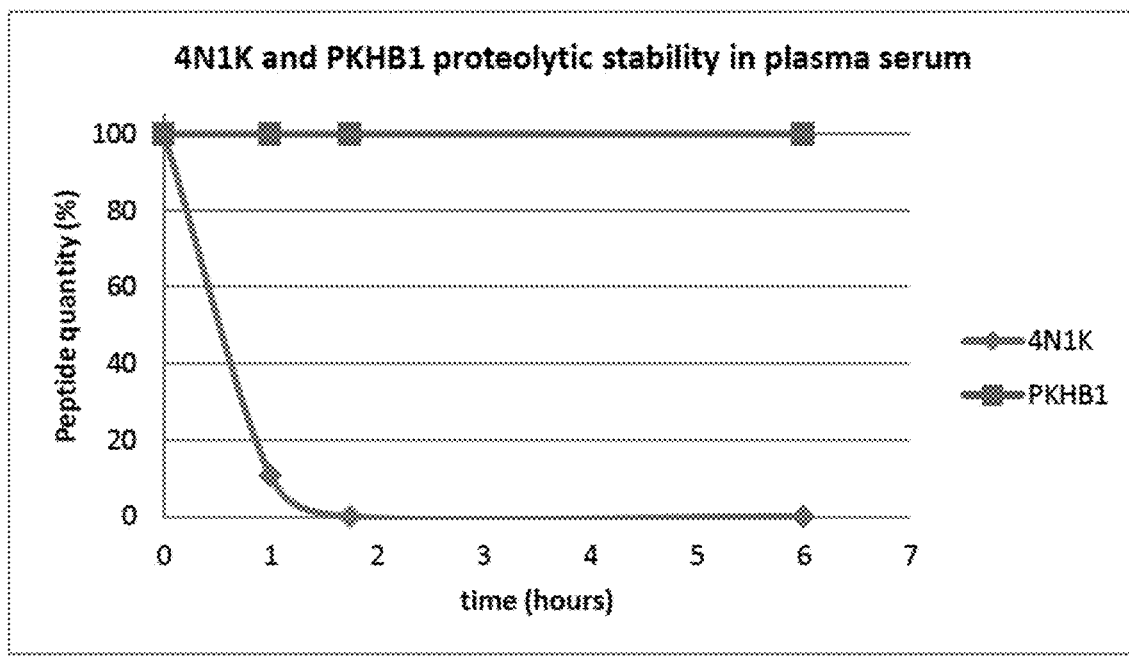

The inventors demonstrate that CD47 ligation by 4N1K (SEQ ID NO:1), a soluble and monovalent decapeptide that mimics the C-terminal domain of TSP-1, induces caspase-independent PCD in B-chronic lymphocytic leukemia (CLL) primary cells. Contrary to the anti-CD47 mAb which needs to be immobilized to induced PCD, the soluble 4N1K peptide does not need to be coated on plastic to induce caspase-independent PCD. A negative control peptide 4NGG (SEQ ID NO:2-4N1K mutated in two amino acids-) is unable to induce PCD, signifying the specificity of the 4N1K PCD induction (FIG. 1). Moreover, CD47 ligation by 4N1K and its derivative PKHB1 specifically eliminates leukemic B-cells, and not healthy B-lymphocytes or resting normal B-cells from CLL patients (FIGS. 2, 5 and 6) and represents a better means of inducing death than caspase-dependent PCD (this form of death is effective even in CLL cells from drug refractory individuals bearing deletion on 17p13 or 11q22-q23: ATM/TP53 inactivated-, FIG. 2). In vivo mouse studies fully confirm the specificity of this peptide strategy in inducing PCD in leukemic cells (FIGS. 7 and 8).

Thus, the invention relates to a soluble peptide comprising the amino acids sequence: KRFYVVMWKK (SEQ ID NO:1) or a function-conservative variant thereof for use in the treatment of cancer.

The invention also relates to a pharmaceutical composition for use in the treatment of cancer comprising at least one soluble peptide according to the invention or at least one acid nucleic according to the invention or at least one expression vector according to the invention, or at least one host cell according to the invention and a pharmaceutically acceptable carrier.

DETAILED DESCRIPTION OF THE INVENTION

Peptide and Uses Thereof

A first object of the invention relates to a soluble peptide comprising the amino acids sequence: KRFYVVMWKK (SEQ ID NO:1) or a function-conservative variant thereof for use in the treatment of cancer.

The invention also encompasses peptides that are function-conservative variants of the soluble peptide comprising SEQ ID NO: 1 as described here above.

In one embodiment, the soluble peptide according to the invention may differ from 1, 2 or 3 amino acids to the SEQ ID NO:1.

In another embodiment, the soluble peptide according to the invention may differ from 4 or 5 amino acids to the SEQ ID NO:1.

In one embodiment, the soluble peptide of the invention comprises at least 75% identity over said the SEQ ID NO: 1, even more preferably at least 80%, at least 85%, at least 90%, at least 95%, at least 97% and is still able to decrease tumor cell proliferation or still able to induce PCD in tumor cell.

In one embodiment, the soluble peptide of the invention consists in the amino acid sequence as set forth in SEQ ID NO:1 or a variant thereof comprising at least 75%, preferably at least 80%, 85%, 90%, 95%, 96%, 97%, 98%, 99%, 99.5% or 99.9% identity with SEQ ID NO:1 and is still able to decrease tumor cell proliferation or still able to induce PCD in tumor cells.

To verify whether the newly generated soluble peptides induce the same type of caspase-independent PCD than the initially characterized peptide 4N1K a flow cytometry analysis (such as described in FIG. 2) may be performed with each peptide. A comparison of the results obtained in treatments with/without the caspase inhibitor Z-VAD.fmk will corroborate that the mode of cell death induced by the 4N1K-derived peptides is caspase-independent. Additionally, a time-course and a dose-response performed in different tumor cells will determine the optimal conditions for each peptide and each malignant cell type.

In one embodiment of the invention, said soluble peptide is an amino acid sequence of less than 50 amino acids long that comprises the amino acid sequence SEQ ID NO:1 as defined here above.

In another embodiment of the invention, said soluble peptide is an amino acid sequence of less than 45 amino acids long that comprises the amino acid sequence SEQ ID NO:1 as defined here above.

In another embodiment of the invention, said soluble peptide is an amino acid sequence of less than 40 amino acids long that comprises the amino acid sequence SEQ ID NO:1 as defined here above.

In another embodiment of the invention, said soluble peptide is an amino acid sequence of less than 30 amino acids long that comprises the amino acid sequence SEQ ID NO:1 as defined here above.

In another embodiment of the invention, said soluble peptide is an amino acid sequence of less than 20 amino acids long that comprises the amino acid sequence SEQ ID NO:1 as defined here above.

In another embodiment of the invention, said soluble peptide is an amino acid sequence of less than 15 amino acids long that comprises the amino acid sequence SEQ ID NO:1 as defined here above.

As used herein, the term "Function-conservative variants" refer to those in which a given amino acid residue in a protein or enzyme has been changed (inserted, deleted or substituted) without altering the overall conformation and function of the peptide. Such variants include protein having amino acid alterations such as deletions, insertions and/or substitutions. A "deletion" refers to the absence of one or more amino acids in the protein. An "insertion" refers to the addition of one or more of amino acids in the protein. A "substitution" refers to the replacement of one or more amino acids by another amino acid residue in the protein. Typically, a given amino acid is replaced by an amino acid having similar properties (such as, for example, polarity, hydrogen bonding potential, acidic, basic, hydrophobic, aromatic, and the like). This given amino acid can be a natural amino acid or a non natural amino acid. Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared. Two amino acid sequences are "substantially homologous" or "substantially similar" when greater than 80%, preferably greater than 85%, preferably greater than 90% of the amino acids are identical, or greater than about 90%, preferably greater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

Typically, the invention encompasses soluble peptides substantially identical to the soluble peptide comprising SEQ ID NO:1 in which one or more residues have been conservatively substituted with a functionally similar residue and which displays the functional aspects of the soluble peptides comprising SEQ ID NO:1 as described here above, i.e. being still able to decrease tumor cell proliferation in substantially the same way as a peptide consisting of the given amino acid sequence.

Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid or another.

The term "conservative substitution" also includes the use of a chemically derivatized residue in place of a non-derivatized residue. "Chemical derivative" refers to a subject peptide having one or more residues chemically derivatized by reaction of a functional side group. Examples of such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Chemical derivatives also include peptides that contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. The term "conservative substitution" also includes the use of non natural amino acids aimed to control and stabilize peptides or proteins secondary structures. These non natural amino acids are chemically modified amino acids such as prolinoamino acids, beta-amino acids, N-methylamino acids, cyclopropylamino acids, alpha,alpha-substituted amino acids as describe here below. These non natural amino acids may include also fluorinated, chlorinated, brominated- or iodinated modified amino acids.

In one embodiment, soluble peptides of the invention may be as described in example 2.

In another embodiment, the soluble peptide of the invention is the PKHB1 peptide as describe in examples 2 and 3.

In another embodiment, the soluble peptide of the invention is the PKHB3 peptide as describe in example 2.

In another embodiment, the soluble peptide of the invention is the PKHB4 peptide as describe in example 2.

In another embodiment, the soluble peptide of the invention is the PKHB9 peptide as describe in example 2.

In another embodiment, the soluble peptide of the invention is the PKHB10 peptide as describe in example 2.

In another embodiment, the soluble peptide of the invention is the PKHB11 peptide as describe in example 2.

In one embodiment, soluble peptides of the invention may comprise a tag. A tag is an epitope-containing sequence which can be useful for the purification of the soluble peptides. It is attached to by a variety of techniques such as affinity chromatography, for the localization of said peptide or polypeptide within a cell or a tissue sample using immunolabeling techniques, the detection of said peptide or polypeptide by immunoblotting etc. Examples of tags commonly employed in the art are the GST (glutathion-S-transferase)-tag, the FLAG™-tag, the Strep-tag™, V5 tag, myc tag, His tag etc.

In one embodiment, soluble peptides of the invention may be labelled by a fluorescent dye. Dye-labelled fluorescent peptides are important tools in cellular studies. Peptides can be labelled on the N-terminal side or on the C-terminal side.

N-Terminal Peptide Labeling Using Amine-Reactive Fluorescent Dyes:

Amine-reactive fluorescent probes are widely used to modify peptides at the N-terminal or lysine residue. A number of fluorescent amino-reactive dyes have been developed to label various peptides, and the resultant conjugates are widely used in biological applications. Three major classes of amine-reactive fluorescent reagents are currently used to label peptides: succinimidyl esters (SE), isothiocyanates and sulfonyl chlorides.

C-Terminal Labeling Using Amine-Containing Fluorescent Dyes:

Amine-containing dyes are used to modify peptides using water-soluble carbodiimides (such as EDC) to convert the carboxy groups of the peptides into amide groups. Either NHS or NHSS may be used to improve the coupling efficiency of EDC-mediated protein-carboxylic acid conjugations.

Labelled peptides derived from 4N1K have the following general formula:

potentially important therapeutic compounds can be decreased significantly by combination with a variety of drug carrier vehicles that modify biodistribution.

A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain.

Polyethylene glycol (PEG) has been widely used as a drug carrier, given its high degree of biocompatibility and ease of modification. Attachment to various drugs, proteins, and liposomes has been shown to improve residence time and

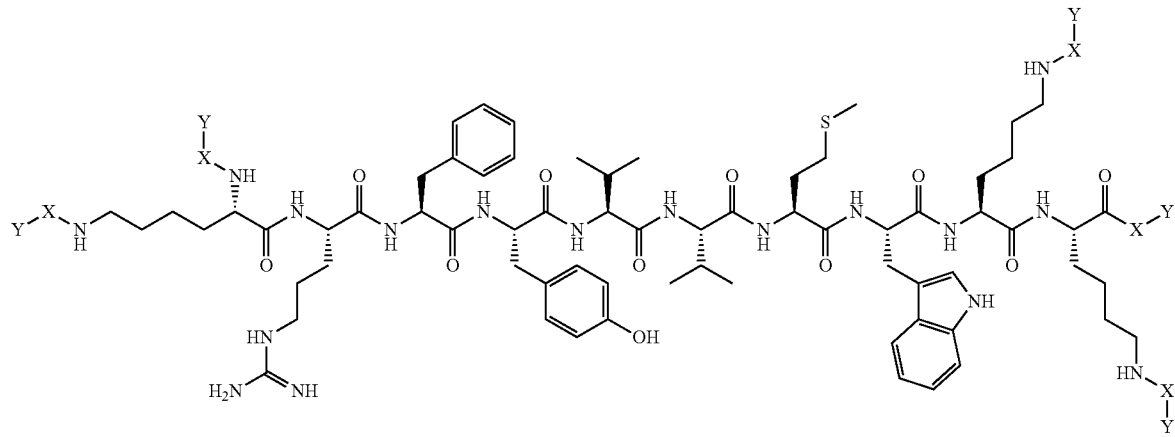

Where X and/or Y can be nothing or hydrogen and/or spacers and/or fluorescent dyes.

PKHB8 (formula (VII)) is an example of peptide from this series where a spacer formed by two beta-alanine residues and a fluorescent dye (fluorescein) have been introduced on the N-terminal side of the peptide, on the alpha-amino group of the lysine residue:

decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of Formula (VII)

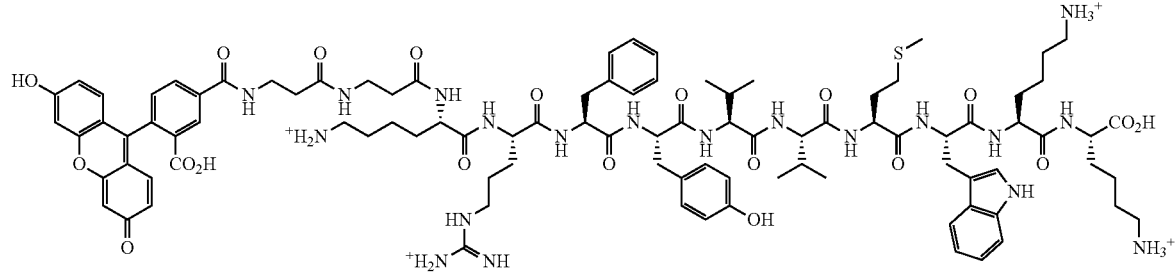

In another embodiment, the soluble peptide of the invention is the PKHB8 peptide.

In specific embodiments, it is contemplated that soluble peptides used in the therapeutic methods of the present invention may be modified in order to improve their therapeutic efficacy. Such modification of therapeutic compounds may be used to decrease toxicity, increase circulatory time, or modify biodistribution. For example, the toxicity of numerous attachment points per molecule (providing greater drug loading), and which could be synthetically designed to suit a variety of applications.

Those of skill in the art are aware of PEGylation techniques for the effective modification of drugs. For example, drug delivery polymers that consist of alternating polymers of PEG and tri-functional monomers such as lysine have been used by VectraMed (Plainsboro, N.J.). The PEG chains (typically 2000 daltons or less) are linked to the a- and e-amino groups of lysine through stable urethane linkages. Such copolymers retain the desirable properties of PEG, while providing reactive pendent groups (the carboxylic acid groups of lysine) at strictly controlled and predetermined intervals along the polymer chain. The reactive pendent groups can be used for derivatization, cross-linking, or conjugation with other molecules. These polymers are useful in producing stable, long-circulating pro-drugs by varying the molecular weight of the polymer, the molecular weight of the PEG segments, and the cleavable linkage between the drug and the polymer. The molecular weight of the PEG segments affects the spacing of the drug/linking group complex and the amount of drug per molecular weight of conjugate (smaller PEG segments provides greater drug loading). In general, increasing the overall molecular weight of the block co-polymer conjugate will increase the circulatory half-life of the conjugate. Nevertheless, the conjugate must either be readily degradable or have a molecular weight below the threshold-limiting glomular filtration (e.g., less than 45 kDa).

In addition, to the polymer backbone being important in maintaining circulatory half-life, and biodistribution, linkers may be used to maintain the therapeutic agent in a pro-drug form until released from the backbone polymer by a specific trigger, typically enzyme activity in the targeted tissue. For example, this type of tissue activated drug delivery is particularly useful where delivery to a specific site of biodistribution is required and the therapeutic agent is released at or near the site of pathology. Linking group libraries for use in activated drug delivery are known to those of skill in the art and may be based on enzyme kinetics, prevalence of active enzyme, and cleavage specificity of the selected disease-specific enzymes (see e.g., technologies of established by VectraMed, Plainsboro, N.J.). Such linkers may be used in modifying the soluble peptides-derived described herein for therapeutic delivery.

According to the invention, soluble peptides may be produced by conventional automated peptide synthesis methods or by recombinant expression. General principles for designing and making proteins are well known to those of skill in the art.

Soluble peptides of the invention may be synthesized in solution or on a solid support in accordance with conventional techniques. Various automatic synthesizers are commercially available and can be used in accordance with known protocols as described in Stewart and Young; Tam et al., 1983; Merrifield, 1986 and Barany and Merrifield, Gross and Meienhofer, 1979. Soluble peptides of the invention may also be synthesized by solid-phase technology employing an exemplary peptide synthesizer such as a Model 433A from Applied Biosystems Inc. The purity of any given protein; generated through automated peptide synthesis or through recombinant methods may be determined using reverse phase HPLC analysis. Chemical authenticity of each peptide may be established by any method well known to those of skill in the art.

As an alternative to automated peptide synthesis, recombinant DNA technology may be employed wherein a nucleotide sequence which encodes a protein of choice is inserted into an expression vector, transformed or transfected into an appropriate host cell and cultivated under conditions suitable for expression as described herein below. Recombinant methods are especially preferred for producing longer polypeptides.

A variety of expression vector/host systems may be utilized to contain and express the peptide or protein coding sequence. These include but are not limited to microorganisms such as bacteria transformed with recombinant bacteriophage, plasmid or cosmid DNA expression vectors; yeast transformed with yeast expression vectors (Giga-Hama et al., 1999); insect cell systems infected with virus expression vectors (e.g., baculovirus, see Ghosh et al., 2002); plant cell systems transfected with virus expression vectors (e.g., cauliflower mosaic virus, CaMV; tobacco mosaic virus, TMV) or transformed with bacterial expression vectors (e.g., Ti or pBR322 plasmid; see e.g., Babe et al., 2000); or animal cell systems. Those of skill in the art are aware of various techniques for optimizing mammalian expression of proteins, see e.g., Kaufman, 2000; Colosimo et al., 2000. Mammalian cells that are useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells. Exemplary protocols for the recombinant expression of the peptide substrates or fusion polypeptides in bacteria, yeast and other invertebrates are known to those of skill in the art and a briefly described herein below. U.S. Pat. Nos. 6,569,645; 6,043,344; 6,074,849; and 6,579,520 provide specific examples for the recombinant production of soluble peptides and these patents are expressly incorporated herein by reference for those teachings. Mammalian host systems for the expression of recombinant proteins also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, and the like have specific cellular machinery and characteristic mechanisms for such post-translational activities and may be chosen to ensure the correct modification and processing of the introduced, foreign protein.

In the recombinant production of the soluble peptides-derived of the invention, it would be necessary to employ vectors comprising polynucleotide molecules for encoding the soluble peptides-derived. Methods of preparing such vectors as well as producing host cells transformed with such vectors are well known to those skilled in the art. The polynucleotide molecules used in such an endeavor may be joined to a vector, which generally includes a selectable marker and an origin of replication, for propagation in a host. These elements of the expression constructs are well known to those of skill in the art. Generally, the expression vectors include DNA encoding the given protein being operably linked to suitable transcriptional or translational regulatory sequences, such as those derived from a mammalian, microbial, viral, or insect genes. Examples of regulatory sequences include transcriptional promoters, operators, or enhancers, mRNA ribosomal binding sites, and appropriate sequences which control transcription and translation.

The terms "expression vector," "expression construct" or "expression cassette" are used interchangeably throughout this specification and are meant to include any type of genetic construct containing a nucleic acid coding for a gene product in which part or all of the nucleic acid encoding sequence is capable of being transcribed.

The choice of a suitable expression vector for expression of the peptides or polypeptides of the invention will of course depend upon the specific host cell to be used, and is within the skill of the ordinary artisan. Methods for the construction of mammalian expression vectors are disclosed, for example, in Okayama and Berg, 1983; Cosman et al., 1986; Cosman et al., 1984; EP-A-0367566; and WO 91/18982. Other considerations for producing expression vectors are detailed in e.g., Makrides et al., 1999; Kost et al., 1999. Wurm et al., 1999 is incorporated herein as teaching factors for consideration in the large-scale transient expression in mammalian cells for recombinant protein production.

Expression requires that appropriate signals be provided in the vectors, such as enhancers/promoters from both viral and mammalian sources that may be used to drive expression of the nucleic acids of interest in host cells. Usually, the nucleic acid being expressed is under transcriptional control of a promoter. A "promoter" refers to a DNA sequence recognized by the synthetic machinery of the cell, or introduced synthetic machinery, required to initiate the specific transcription of a gene. Nucleotide sequences are operably linked when the regulatory sequence functionally relates to the DNA encoding the peptide of interest (i.e., 4N1K, a variant and the like). Thus, a promoter nucleotide sequence is operably linked to a given DNA sequence if the promoter nucleotide sequence directs the transcription of the sequence.

Similarly, the phrase "under transcriptional control" means that the promoter is in the correct location and orientation in relation to the nucleic acid to control RNA polymerase initiation and expression of the gene. Any promoter that will drive the expression of the nucleic acid may be used. The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter. Common promoters include, e.g., the human cytomegalovirus (CMV) immediate early gene promoter, the SV40 early promoter, the Rous sarcoma virus long terminal repeat, [beta]-actin, rat insulin promoter, the phosphoglycerol kinase promoter and glyceraldehyde-3-phosphate dehydrogenase promoter, all of which are promoters well known and readily available to those of skill in the art, can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient to produce a recoverable yield of protein of interest. By employing a promoter with well known properties, the level and pattern of expression of the protein of interest following transfection or transformation can be optimized. Inducible promoters also may be used.

Another regulatory element that is used in protein expression is an enhancer. These are genetic elements that increase transcription from a promoter located at a distant position on the same molecule of DNA. Where an expression construct employs a cDNA insert, one will typically desire to include a polyadenylation signal sequence to effect proper polyadenylation of the gene transcript. Any polyadenylation signal sequence recognized by cells of the selected transgenic animal species is suitable for the practice of the invention, such as human or bovine growth hormone and SV40 polyadenylation signals.

Acids Nucleic, Vectors, Recombinant Host Cells and Uses Thereof

Another object of the invention relates to a nucleic acid encoding an amino acids sequence comprising SEQ ID NO: 1 or a function-conservative variant thereof as described here above for use in the prevention or treatment of cancer.

In one embodiment, said nucleic acid encoding an amino acids sequence consisting on SEQ ID NO: 1.

Nucleic acids of the invention may be produced by any technique known per se in the art, such as, without limitation, any chemical, biological, genetic or enzymatic technique, either alone or in combination(s).

Another object of the invention is an expression vector comprising a nucleic acid sequence encoding an amino sequence comprising SEQ ID NO: 1 or a function-conservative variant thereof as described here above for use in the prevention or treatment of cancer.

According to the invention, expression vectors suitable for use in the invention may comprise at least one expression control element operationally linked to the nucleic acid sequence. The expression control elements are inserted in the vector to control and regulate the expression of the nucleic acid sequence. Examples of expression control elements include, but are not limited to, lac system, operator and promoter regions of phage lambda, yeast promoters and promoters derived from polyoma, adenovirus, retrovirus, lentivirus or SV40. Additional preferred or required operational elements include, but are not limited to, leader sequence, termination codons, polyadenylation signals and any other sequences necessary or preferred for the appropriate transcription and subsequent translation of the nucleic acid sequence in the host system. It will be understood by one skilled in the art that the correct combination of required or preferred expression control elements will depend on the host system chosen. It will further be understood that the expression vector should contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods or commercially available.

Another object of the invention is a host cell comprising an expression vector as described here above for use in the prevention or treatment of cancer.

According to the invention, examples of host cells that may be used are eukaryote cells, such as animal, plant, insect and yeast cells and prokaryotes cells, such as E. coli. The means by which the vector carrying the gene may be introduced into the cells include, but are not limited to, microinjection, electroporation, transduction, or transfection using DEAE-dextran, lipofection, calcium phosphate or other procedures known to one skilled in the art.

In another embodiment, eukaryotic expression vectors that function in eukaryotic cells are used. Examples of such vectors include, but are not limited to, viral vectors such as retrovirus, adenovirus, adeno-associated virus, herpes virus, vaccinia virus, poxvirus, poliovirus; lentivirus, bacterial expression vectors, plasmids, such as pcDNA3 or the baculovirus transfer vectors. Preferred eukaryotic cell lines include, but are not limited to, COS cells, CHO cells, HeLa cells, NIH/3T3 cells, 293 cells (ATCC # CRL1573), T2 cells, dendritic cells, or monocytes.

Therapeutic Methods

In a particular embodiment, soluble peptides, nucleic acids, expression vector or host cells of the invention may be useful in the treatment of a cancer selected form the group consisting of adrenal cortical cancer, anal cancer, bile duct cancer, bladder cancer, bone cancer, brain and central nervous system cancer, breast cancer, Castleman disease, cervical cancer, colorectal cancer, endometrial cancer, esophagus cancer, gallbladder cancer, gastrointestinal carcinoid tumors, Hodgkin's disease, non-Hodgkin's lymphoma, Kaposi's sarcoma, kidney cancer, laryngeal and hypopharyngeal cancer, liver cancer, lung cancer, mesothelioma, plasmacytoma, nasal cavity and paranasal sinus cancer, nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma, salivary gland cancer, skin cancer, stomach cancer, testicular cancer, thymus cancer, thyroid cancer, vaginal cancer, vulvar cancer, and uterine cancer.

In another particular embodiment, soluble peptides, nucleic acids, expression vector or host cells of the invention may be useful in the prevention and the treatment of leukemia and particularly in acute lymphoblastic leukemia, B-chronic lymphocytic leukemia, hairy-cell leukemia, adult T-cell leukemia, prolymophocytic leukaemia of T-cell type or myeloid leukaemia.

In one embodiment, the leukemia is a B-chronic lymphocytic leukemia (CLL).

In a particular embodiment, soluble peptides, nucleic acids, expression vector or host cells of the invention may be useful in the treatment of a refractory CLL. In another particular embodiment, soluble peptides, nucleic acids, expression vector or host cells of the invention may be useful in the treatment of a refractory CLL with poor prognosis, including unmutated IGHV, complex karyotype and dysfunctional or mutated TP53, ATM, NOTH1, MYD88, XPO1, KLHL6, SF3B1, POT1 and BIRC3 B-cells.

As used herein, the term "refractory CLL" denotes a CLL refractory to common treatments used against leukemia (described in pages 2 and 3).

In a particular embodiment, soluble peptides, nucleic acids, expression vector or host cells of the invention may be useful in the treatment of refractory CLL that present intrinsic mutations that could allow to drug resistance (e.g, mutation/deletions in TP53, ATM, NOTH1, MYD88, XPO1, KLHL6, SF3B1, POT1 and BIRC3 genes or refractory to the treatments described in pages 2 and 3).

In a particular embodiment, soluble peptides, nucleic acids, expression vector or host cells of the invention may be useful in the treatment of refractory CLL where common treatment like anti-CD20, fludarabine or cladribine are not working.

Another object of the invention relates to a method for treating cancer comprising administering to a subject in need thereof a therapeutically effective amount of soluble peptides as described above or a nucleic acid according to the invention or an expression vector according to the invention or a host cell according to the invention.

In one aspect, the invention relates to a method for treating cancer comprising administering to a subject in need thereof a therapeutically effective amount of soluble peptide of SEQ ID NO:1 or a function-conservative variant thereof as above described.

In another embodiment, the invention relates to a method for treating cancer comprising administering to a subject in need thereof a therapeutically effective amount of a soluble peptide according to the invention.

As used herein, the term "therapeutically effective amount" is intended for a minimal amount of active agent, which is necessary to impart therapeutic benefit to a subject. For example, a "therapeutically effective amount of the active agent" to a subject is an amount of the active agent that induces, ameliorates or causes an improvement in the pathological symptoms, disease progression, or physical conditions associated with the disease affecting the subject.

As used herein, the term "treating" a disorder or a condition refers to reversing, alleviating or inhibiting the process of one or more symptoms of such disorder or condition.

As used herein, the term "subject" denotes a mammal, such as a rodent, a feline, a canine, and a primate. Preferably a subject according to the invention is a human.

Pharmaceutical Composition

Another object of the invention is a pharmaceutical composition for use in the treatment of cancer comprising:
 a) at least one soluble peptide according to the invention; or
 b) at least one acids nucleic according to the invention; or
 c) at least one expression vector according to the invention or;
 d) at least one host cell according to the invention;
 e) and a pharmaceutically acceptable carrier.

In one embodiment, said pharmaceutical composition comprises at least one soluble peptide having the sequence SEQ ID NO: 1.

In another embodiment, said pharmaceutical composition comprises a function-conservative variant thereof of the peptide having the sequence SEQ ID NO: 1.

In still another embodiment, said pharmaceutical composition comprises the peptide PKHB1.

Any therapeutic agent of the invention as above described may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, intranasal, intraocular, intravenous, intramuscular or subcutaneous administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of a polypeptide or a nucleic acid according to the invention may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, mixtures thereof and in oils. Under ordinary conditions of storage and use, these preparations contain a preservative to prevent the growth of microorganisms.

The peptides thereof or the nucleic acid according to the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution may be suitably buffered and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

In addition to the compounds formulated for parenteral administration, such as intravenous or intramuscular injection, other pharmaceutically acceptable forms include, e.g. tablets or other solids for oral administration; time release capsules; and any other form currently used.

In one embodiment, the pharmaceutical composition may comprise cells stably expressing a peptide or variant thereof according to the invention. For example, the pharmaceutical composition may comprise HEK293T cells stably expressing the peptide of the invention polypeptide, or HCT116 cells stably expressing the peptide of the invention. The cells may be encapsulated in alginate gel beads, as described in Desille et al., 2001, 2002 and Mahler et al., 2003. This vectorization approach enables a localized delivery of the polypeptide of the invention.

Compositions of the present invention may comprise a further therapeutic active agent. The present invention also relates to a kit comprising a polypeptide or a nucleic acid according to the invention and a further therapeutic active agent.

In one embodiment said therapeutic active agent is an anticancer agent. For example, said anticancer agents include but are not limited to fludarabine, gemcitabine, capecitabine, methotrexate, taxol, taxotere, mercaptopurine, thioguanine, hydroxyurea, cytarabine, cyclophosphamide, ifosfamide, nitrosoureas, platinum complexes such as cisplatin, carboplatin and oxaliplatin, mitomycin, dacarbazine, procarbizine, etoposide, teniposide, campathecins, bleomycin, doxorubicin, idarubicin, daunorubicin, dactinomycin, plicamycin, mitoxantrone, L-asparaginase, doxorubicin, epimbicm, 5-fluorouracil, taxanes such as docetaxel and paclitaxel, leucovorin, levamisole, irinotecan, estramustine, etoposide, nitrogen mustards, BCNU, nitrosoureas such as carmustme and lomustine, vinca alkaloids such as vinblastine, vincristine and vinorelbine, imatimb mesylate, hexamethyhnelamine, topotecan, kinase inhibitors, phosphatase inhibitors, ATPase inhibitors, tyrphostins, protease inhibitors, inhibitors herbimycm A, genistein, erbstatin, and lavendustin A. In one embodiment, additional anticancer agents may be selected from, but are not limited to, one or a combination of the following class of agents: alkylating agents, plant alkaloids, DNA topoisomerase inhibitors, antifolates, pyrimidine analogs, purine analogs, DNA antimetabolites, taxanes, podophyllotoxin, hormonal therapies, retinoids, photosensitizers or photodynamic therapies, angiogenesis inhibitors, antimitotic agents, isoprenylation inhibitors, cell cycle inhibitors, actinomycins, bleomycins, anthracyclines, MDR inhibitors and Ca2+ ATPase inhibitors.

Additional anticancer agents may be selected from, but are not limited to, cytokines, chemokines, growth factors, growth inhibitory factors, hormones, soluble receptors, decoy receptors, monoclonal or polyclonal antibodies, mono-specific, bi-specific or multi-specific antibodies, monobodies, polybodies.

Additional anticancer agent may be selected from, but are not limited to, growth or hematopoietic factors such as erythropoietin and thrombopoietin, and growth factor mimetics thereof.

In the present methods for treating cancer the further therapeutic active agent can be an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoemanolamine, alizapride, azasetron, benzquinamide, bietanautine, bromopride, buclizine, clebopride, cyclizine, dunenhydrinate, diphenidol, dolasetron, meclizme, methallatal, metopimazine, nabilone, oxypemdyl, pipamazine, scopolamine, sulpiride, tetrahydrocannabinols, thiefhylperazine, thioproperazine and tropisetron. In a particular embodiment, the antiemetic agent is granisetron or ondansetron.

In another embodiment, the further therapeutic active agent can be an hematopoietic colony stimulating factor. Suitable hematopoietic colony stimulating factors include, but are not limited to, filgrastim, sargramostim, molgramostim and epoietin alpha.

In still another embodiment, the other therapeutic active agent can be an opioid or non-opioid analgesic agent. Suitable opioid analgesic agents include, but are not limited to, morphine, heroin, hydromorphone, hydrocodone, oxymorphone, oxycodone, metopon, apomorphine, nomioiphine, etoipbine, buprenorphine, mepeddine, lopermide, anileddine, ethoheptazine, piminidine, betaprodine, diphenoxylate, fentanil, sufentanil, alfentanil, remifentanil, levorphanol, dextromethorphan, phenazodne, pemazocine, cyclazocine, methadone, isomethadone and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam and sulindac.

In yet another embodiment, the further therapeutic active agent can be an anxiolytic agent. Suitable anxiolytic agents include, but are not limited to, buspirone, and benzodiazepines such as diazepam, lorazepam, oxazapam, chlorazepate, clonazepam, chlordiazepoxide and alprazolam.

The invention will be further illustrated by the following figures and examples. However, these examples and figures should not be interpreted in any way as limiting the scope of the present invention.

FIGURES

FIG. 1. B cells isolated from 35 different CLL patients (including patients with intrinsic resistance to the current therapeutics, including unmutated IGHV, complex karyotype and dysfunctional TP53 or ATM genes) were cultured 1 h in the presence of an immobilized CD47 mAb (clone B6H12), the soluble TSP-1-derived peptide 4N1K (300 µM), or the negative soluble control peptide 4NGG (4N1K mutated in two amino acids; sequence: KRFYGGMWKK, SEQ ID NO:2). The percentage of cells that expose phosphatidylserine (measured with Annexin-V-FITC) was recorded and expressed as a plot.

Figure 2A:
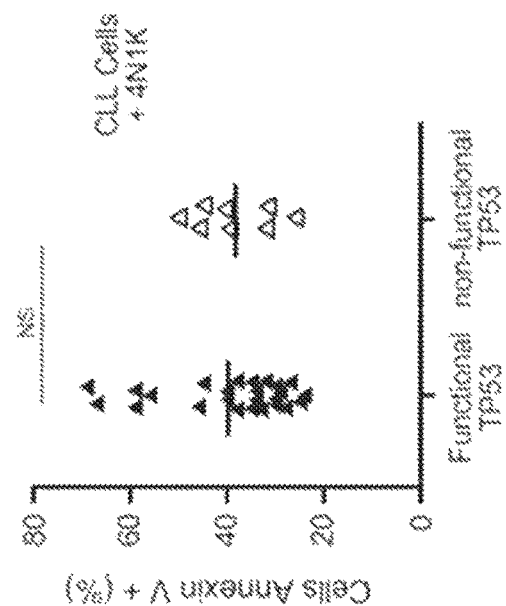
Figure 2B:
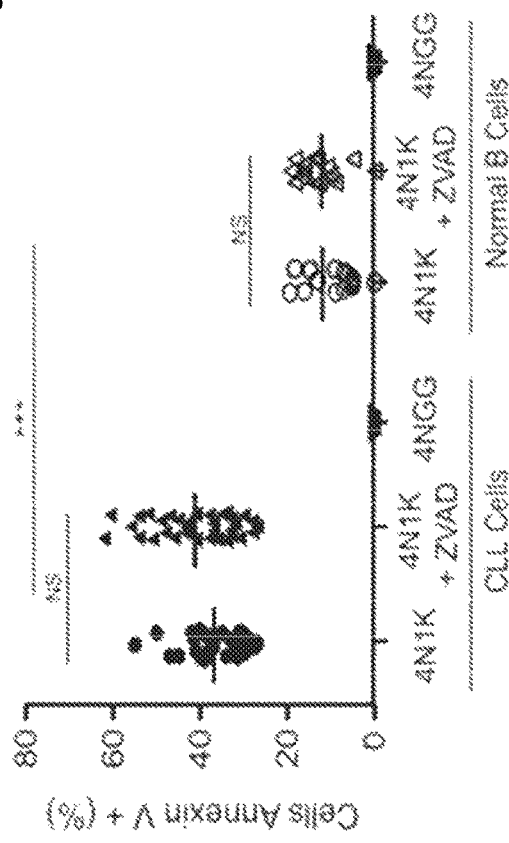

FIG. 2A-B. FIG. 2(A) B cells isolated from a panel CLL patients or from control volunteers were pre-incubated (1 h) or not with 50 µM of the broad caspase inhibitor z-VAD.fmk and cultured 1 h in the presence of 4N1K (300 µM) or the negative control peptide 4NGG (4N1K mutated in two amino acids; sequence: KRFYGGMWKK, SEQ ID NO:2). The percentage of cells that expose phosphatidylserine (measured with Annexin-V-FITC) was recorded and expressed as a plot. ***, $p<0.001$ (different response to 4N1K in CLL and normal B cells). NS, Not significant difference in 4N1K-induced PCD between CLL cells treated or not with the caspase inhibitor ZVAD. FIG. 2(B) A panel of B cells from CLL patients, analyzed by functional P53 activity, were cultured 1 h in the presence of 4N1K as above. PCD was measured with Annexin-V-FITC. NS, Not significant difference in PCD response to 4N1K between CLL cells presenting functional and non-functional TP53.

Figure 3:
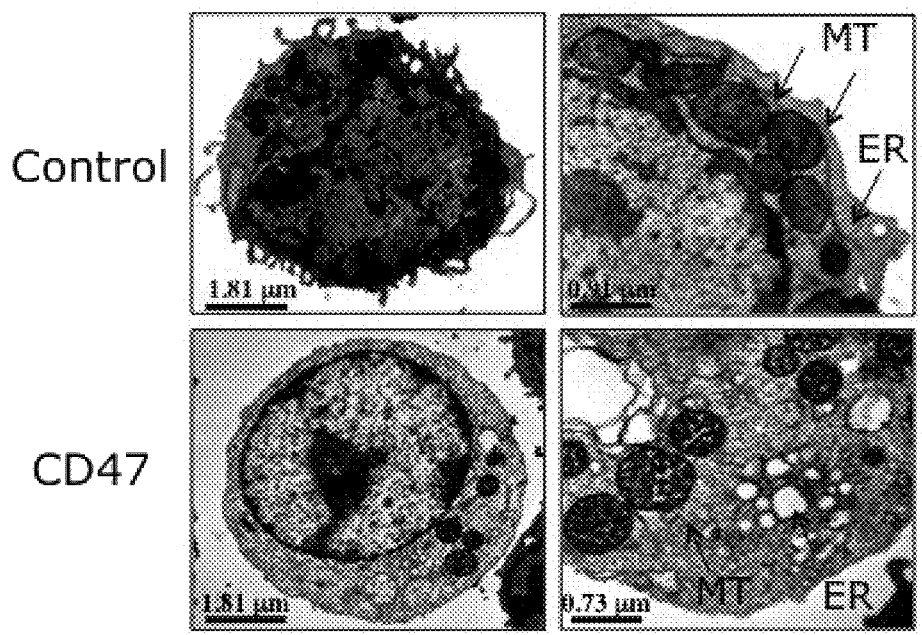

FIG. 3. Electron micrographs of CLL cells untreated (control) or incubated with 4N1K (CD47). Upper panels demonstrate a typical example of the mitochondrial (MT) and ER normal morphology. Lower panels show the mitochondrial morphology and ER dilation observed in CD47 mAb-treated cells.

Figure 4:
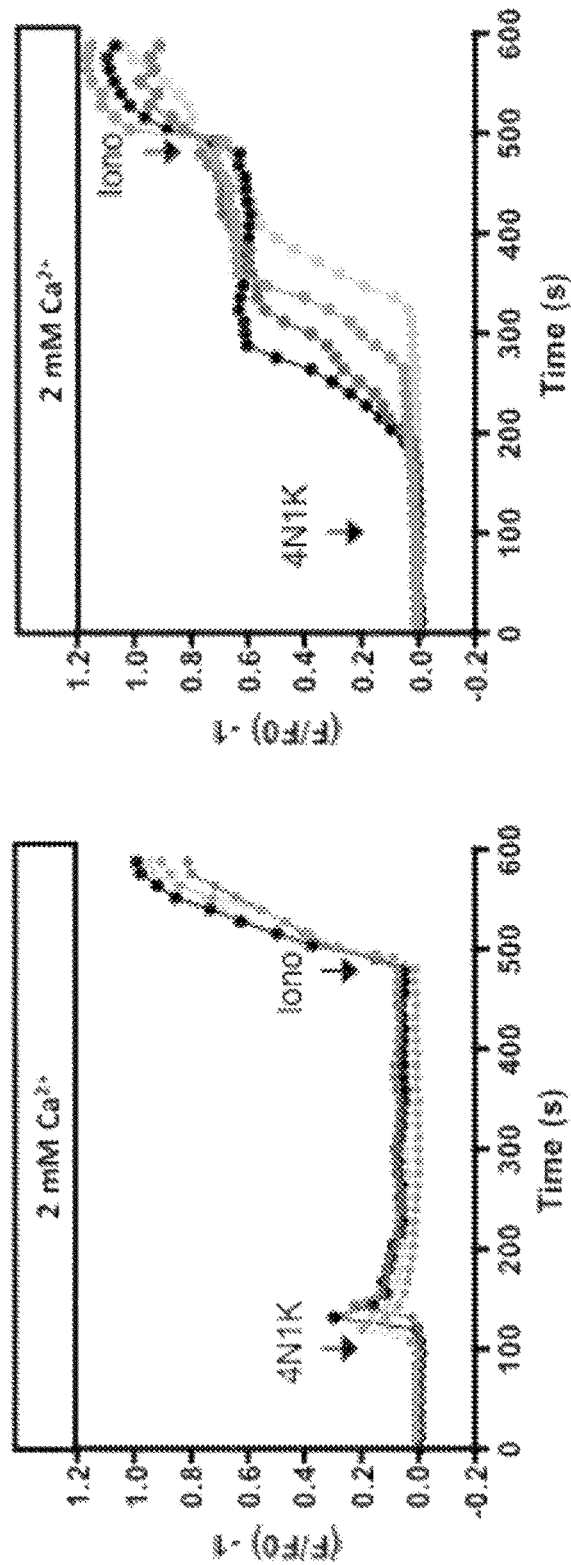

FIG. 4. Free Ca2+ mobilization assessed with Fura-2 AM by Till photonics in B-lymphocytes from control volunteers (n=4; on the left) and B cells from representative CLL patients (n=4; on the right) after CD47 stimulation with 4N1K. Ionomycin (Iono), which was used as a positive control, signals the maximum of Ca2+ monitored. Importantly, in CLL the Ca2+ mobilization induced by 4N1K does not come back to basal level (as observed in normal B cells) and underlined a calcium overload in 4N1K-treated CLL cells.

Figure 5:
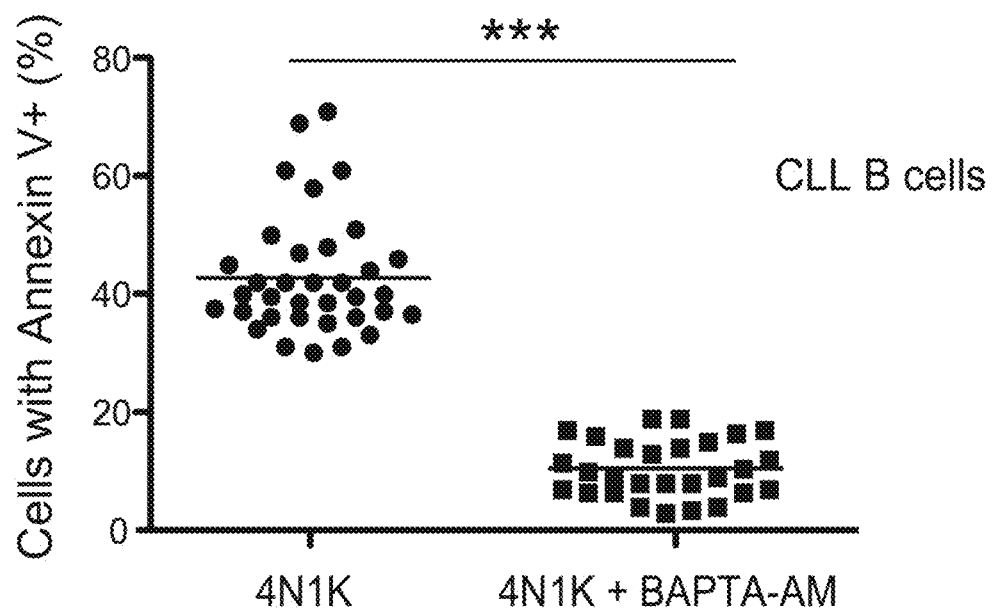

FIG. 5. The same panel of B cells from CLL patients depicted in FIG. 2 was pre-incubated or not with the calcium chelator BAPTA-AM (20 µM) prior to induction of PCD by 4N1K as above. ***, $p<0.001$. Note that the treatment with BAPTA abrogates 4N1K-mediated PCD.

FIG. 6A-D. FIG. 6(A) B cells isolated from CLL patients were left untreated (control) or cultured 1 h in the presence of 4N1K or the 4N1K-derivative peptide PKHB-1 at the indicated concentration. The percentage of cells that expose phosphatidylserine (measured with Annexin-V-FITC) was recorded and expressed as a plot. Data are the means of eight independent experiments. FIG. 6(B) In a similar experiment B-lymphocytes from 14 different CLL patients, including individuals with unmutated IGHV, complex karyotype and dysfunctional TP53, were left untreated (control) or cultured 1 h in the presence of 4N1K (300 µM) or the 4N1K-derivative peptide PKHB-1 (150 µM). PCD was measured by Annexin-V-FITC labelling in a flow cytometer. FIG. 6(C) Cell death was determined as described in A in 4N1K or PKHB1-treated CD19+/CD5− (residual B-cells) and CD19+/CD5+ B-lymphocytes (CLL cells) identified by flow cytometry from each CLL patient. Data are presented as the mean±s.d. (n=8 patients). FIG. 6(D) Cell death was measured by Annexin V-positive staining in 4N1K or PKHB1-treated CLL cells pre-incubated or not with the intracellular calcium chelator BAPTA-AM. Data are presented as the mean±S.D. (n=10 patients).

FIG. 7A-C: FIGS. 7(A and B) NSG mice (n=8 per group) transplanted subcutaneously with MEC-1 cells received three times a week intraperitoneal injection of 4N1K, PKHB1 or PBS (Control). Tumor volume was measured with a calliper and plotted as a graph. FIG. 7(C) Tumor growth after treatments was also visualized in a photograph by glucose uptake 2-DG. Colour scale indicates fluorescence intensity in arbitrary units.

FIG. 8: 4N1K and PKHB1 peptides stability were evaluated in human serum at 37° C. for 6 h. The relative concentrations of the remaining soluble peptides were analyzed by HPLC, by the integration of the absorbance at 220 nm as a function of retention time.

TABLE 1

PCD induction in cancer cell lines

| Cancer | Cell Line | Cell death induction via CD47 |
|---|---|---|
| Acute T cell leukemia | JURKAT | + |
| Acute lymphoblastic leukemia | CEM | + |
| Adenocarcinoma | MDA-MB-231 | + |
| Breast adenocarcinoma | MCF-7 | + |
| Breast adenocarcinoma | AU-565 | + |
| Breast epithelial cells with transformed morphology | HBL-100 | + |
| Burkitt's lymphoma | RAJI | + |
| Burkitt's lymphoma | RAMOS | + |
| B lymphocytic cell line | RPMI 8226 | + |
| B lymphocytic cell line | RPMI 8866 | + |
| Cervical cancer | HELA | + |
| Chronic Lymphocytic Leukemia | MEC-1 | + |
| Diffuse histiocytic lymphoma | U937 | + |
| Immunoblastic B cell lymphoma | JM-1 | + |
| Ovarian Carcinoma | OV10 | + |
| Lung carcinoma | A549 | + |
| Prostate cancer | LNCAP | + |

+ = more than 35% of cell death induction, assessed by Annexin V labeling, after 1 h of stimulation with 400 µM of 4N1K (means of six independent experiments). No cell death was recorded with the control peptide 4NGG.

TABLE 2

PCD induction in primary cancer cells

| Cancer | Cell death induction via CD47 |
|---|---|
| Ovarian carcinoma | + |
| Breast carcinoma | + |
| Colon carcinoma | + |
| Bladder carcinoma | + |
| Glioblastoma | + |
| Hepatocellular carcinoma | + |
| Prostate tumor cells | + |
| Glioma | + |
| Follicular lymphoma | + |
| Mantle cell lymphoma | + |
| Diffuse large B cell lymphoma | + |
| Chronic Lymphocytic Leukemia | + |
| Marginal B cell lymphoma | + |
| Lymphoplasmacytic lymphoma | + |
| Hairy cell leucemia (HCL) | + |
| Acute T cell leukemia | + |

+ = more than 35% of programmed cell death induction via CD47 receptor.

EXAMPLES

Example 1

Use of 4N1K as Therapeutic Compound

Material & Methods

Patients, B-cell Purification, and Culture Conditions.

After authorized consent forms fresh blood samples will be collected from CLL patients diagnosed according to classical morphological and immunophenotypic criteria at Pitié-Salpêtrière Hospital (Service d'Hématologie Biologique). Normal B lymphocytes will be obtained from EFS (Etablisement Français du Sang). The Institutional Ethics Committee at Pitie-Salpetriere Hospital approved the present study. Mononuclear cells were purified from blood samples using a standard Ficoll-Hypaque gradient, and B cells were positively or negatively selected by magnetic beads coupled to anti-CD19 monoclonal antibody (positive selection) or to anti-CD16, CD3, and CD14 monoclonal antibodies (negative depletion) (Miltenyi Biotech). No changes were found in the cell death response of positively or negatively selected cells. Purified B-lymphocytes were cultured in complete medium (RPMI 1640 medium supplemented with 10% fetal calf serum, 2 mM L-glutamine, and 100 U/ml penicillin-streptomycin). Unless specified, reagents were from Sigma-Aldrich.

Cell Death Induction and Inhibition.

To induce cell death B-lymphocytes were cultured 1 h with the TSP-1 derived peptide 4N1K (300 µM; sequence KRFYVVMWKK, SEQ ID NO:1), the negative control peptide 4NGG (300 µM; sequence KRFYGGMWKK, SEQ ID NO:2), the newly developed peptide PKHB1 (150 µM; sequence (D)K-R-F-Y-G-G-M-W-(D)K) (formula I) or an anti-CD47 mAb (in soluble conditions or in immobilized precoated plates; 5 µg/ml; clone B6H12). Alternatively, B-cells were pre-treated for 30 min before the induction of cell death with the calcium chelator BAPTA-AM (20 µM), the caspase-inhibitor Z-VAD.fmk (50 µM).

Flow Cytometry

We used Annexin V-FITC (BD Biosciences) for the assessment of phosphatidylserine (PS) exposure. Data analysis was carried out in a FACSCanto II (BD Biosciences) on the total cell population (10,000 cells). Data were analyzed using FlowJo software (TreeStar).

Ca2+ Measurements.

Cells, adhered in Polylysine coated glass-bottom Petri dishes, were loaded with Fura-2 AM (1 µM/30 min/37° C.). Cells were then excited by wavelengths of 340 and 380 nm and fluorescence emission of several cells was simultaneously recorded at 510 nm at a frequency of 1 Hz using a dual excitation fluorometric imaging system (TILL-Photonics) controlled by TILL-Vision software. Signals were computed into relative ratio units of the fluorescence intensity of the different wavelengths (340/380 nm). Individual fluorescence values were then analyzed with Origin software to normalize the fluorescence with the first value according to the equation (F/F0)−1, where 'F' is the fluorescence at specific time point and 'F0' is the fluorescence at time 0.

Electron Microscopy.

Cells were fixed with 2% glutaraldehyde in phosphate buffer (pH 7.4) for 2 h at RT, washed, and postfixed in 2% OsO4 before being embedded in Durcupan™. Analysis was performed with a transmission electron microscope (Carl Zeiss MicroImaging), on ultrathin sections stained with uranyl acetate and lead citrate.

In Vivo 4N1K and PKHB-1 Treatments in a Localized CLL Xenograft Model.

$3 \times 10^6$ MEC-1 cells were injected subcutaneously into NOD scid gamma (NSG) mice (Charles River). When the tumor volume reached 0.1 cm$^3$, mice were injected intraperitoneally three times per week with 4NIK or PKHB1 (400 µg in 200 µl PBS). Tumor size was measured every 2-3 days with a calliper and tumor volume, calculated using the formula (length×width$^2$)/2, was expressed as mm$^3$. Alternatively, at the end of treatment mice were injected into the sinus retro-orbital with XenoLight RediJect 2-DG-750 Probe (Caliper) to visualize tumor cell glucose uptake, which reflects cell proliferation. Fluorescence was measured by In vivo imaging system FX Pro (Kodak) and pictures were analysed with the Carestream MI software.

Statistical Analysis.

The significance of differences between experimental data was determined using Student's t test for unpaired observations or for comparative analysis of different groups Mann-Whitney test as described, using graphpad prism software.

Results

Effect of 4N1K Peptide on B Cell from CLL Patients:

The inventors have recently identified that the use of the 4N1K peptide (SEQ ID NO:1) which mimics the C-terminal domain of TSP-1, does not needs to be immobilized to induced caspase-independent PCD as compared to the anti-CD47 mAb (FIG. 1), and that even in CLL cells from refractory patients (ATM or TP53 mutated/deleted, which are refractory to the most common drug treatments used against this leukemia, such as anti-CD20, fludarabine or cladribine; FIG. 2).

The previous results of the inventors indicate that CD47-mediated caspase-independent PCD proceeds via the induction of atypically regulated mitochondrial alterations that are independent from the caspase-dependent apoptotic regulators usually blocked in CLL. Indeed, these results on CD47 are the first published incidence of massive mitochondrial alterations induced without the involvement of caspases (FIG. 3). In addition, experiments performed in B cells from control donors and from a large number of CLL patients (more than 150 to date), have shown that CD47 ligation induces cell death rapidly and with a higher efficacy in CLL cells than in normal B cells. And that, even in B-leukemic cells from drug refractory CLL patients.

Caspase-Independent PCD Induced by 4N1K in CLL

1. Intracellular organelles are key elements in the regulation of programmed cell death, the inventors have performed an ultrastructural study of CLL cells after CD47 ligation. After CD47 triggering, the endoplasmic reticulum (ER) dilates and mitochondria swells and undergoes a morphological change (FIG. 3). These alterations, typical hallmarks of the Ca2+-mediated PCD, seem to indicate that mitochondria and ER are interconnected both physically and physiologically, mainly through the calcium ion: (i) Mitochondria, the main source of cellular adenosine triphosphate, also modulate and synchronize ER Ca2+ signaling; (ii) Stimuli that generate inositol 1,4,5-trisphosphate (IP3) cause release of Ca2+ from the ER, which is rapidly taken up by closely juxtaposed mitochondria.

Using Till photonics Imaging Technology, the inventors have confirmed that the ligation of CD47 in CLL cells is followed by an intracellular free Ca2+ mobilization. Strikingly, compared to normal B cells, the recorded intracellular Ca2+ mobilization is stronger and sustained in leukemic B cells but not in normal B-lymphocytes (FIG. 4). Indeed, in CLL, Ca2+ mobilization induced by 4N1K does not come back to the basal level indicating a Ca2+ overload particularly in these cells. These results correlate to the different sensibility of CLL and normal B cells to CD47-mediated PCD (FIG. 2).

2. Pre-treatment of B cells with the intracellular calcium chelator BAPTA-AM blocks CD47-mediated PCD (FIG. 5). This indicates that the Ca2+ released into the cytosol after 4N1K-triggering plays a pivotal role in this type of caspase-independent PCD in CLL cells.

Importantly, when the inventors analyze PCD and intracellular calcium mobilization in CLL cells from patients with a good prognosis and patients with refractory CLL (unmutated IGHV gene status, high levels of thymidine kinase, soluble CD23, CD38, and ZAP-70 expression, and ATM or TP53 mutation/deletion), they find that the cells from patients with a bad prognosis, which are resistant to caspase-dependent PCD induced by anti-CD20, fludarabine or cladribine, present similar levels of CD47-mediated PCD and, consequently, similar levels of intracellular Ca2+ mobilization after CD47-triggering. These results indicate that the calcium pathway enabled by CD47 is functional even in CLL cells from refractory patients (with a defective caspase-dependent PCD pathway). Thus, 4N1K-mediated caspase-independent PCD occurs more efficiently in CLL cells than in B-lymphocytes from healthy donors and represents a better means of inducing death than caspase-dependent PCD.

3. The inventors have shown that the ligation of the CD47 receptor induces PCD more efficiently in CLL cells than in B-lymphocytes from healthy donors and represents a better means of inducing death than caspase-dependent PCD. Thus, the inventors have hypothesized that the Ca2+-mediated caspase-independent PCD pathway induced by CD47 could be used to eliminate in vivo B leukemic cells. To substantiate this hypothesis, the inventors have developed a xenograft mouse model and conducted in vivo experiments (Materials and Methods for details and FIG. 7). Contrary to controls, the IP injection of the CD47-ligand 4N1K derivatives induce a low reduction in tumor volume.

These new findings are particularly interesting given the potential application of a 4N1K derivatives such as PKHB1, therapy as a treatment for CLL. In this way, it is important to note that: (i) the 4N1K derivatives peptides do not exert toxicity in mice, and (ii) 4N1K derivatives-treatment provokes the external exposure of "eat me signals", such as phosphatidylserine or calreticulin (data not shown). This facilitates the subsequent elimination of dying cells by professional phagocytes.

Effect of 4N1K Peptide on Cancer Cell Lines and Primary Cancer Cells:

The inventors show that stimulation with 4N1K induces more than 35% of cell death induction on cancer cell lines and primary cancer cells whereas 4NGG, the control peptide, is inefficient in inducing caspase-independent PCD (Tables 1 and 2).

These results show that the soluble peptide 4N1K derivatives could be used in a large variety of tumor models.

Example 2

Synthesis of New Soluble Peptides

The structure of 4N1K peptide is as followed:

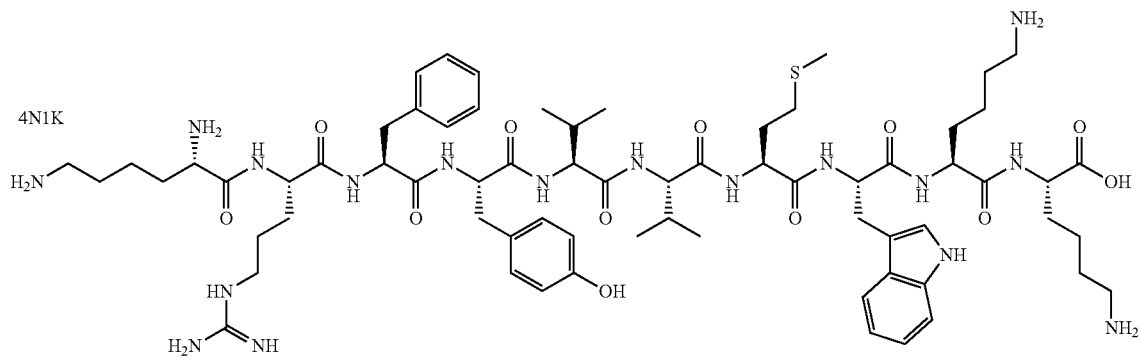 [SMILES: CSCC[C@H](NC(=O)[C@@H](NC(=O)[C@@H](NC(=O)[C@H](Cc1ccc(O)cc1)NC(=O)[C@H](Cc1ccccc1)NC(=O)[C@H](CCCNC(=N)N)NC(=O)[C@@H](N)CCCCN)C(C)C)C(C)C)C(=O)N[C@@H](Cc1c[nH]c2ccccc12)C(=O)N[C@@H](CCCCN)C(=O)N[C@@H](CCCCN)C(=O)O]

4N1K is an undecapeptide with the following sequence: K-R-F-Y-V-V-M-W-K-K (SEQ ID NO:1).

To improve peptide solubility, stability and pharmacological properties, the 4N1K is modified by chemical modifications that are established on the following 2 models:

Model 1

A1—A2—A3—A4—A5—A6—A7—A8—A9—A10

Model 2

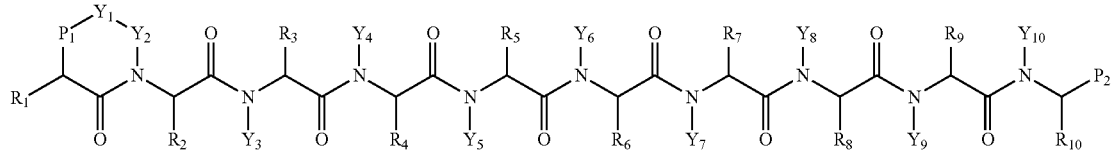

In model peptide 1, A (1 to 10) correspond to nothing and/or natural amino acids and/or non natural amino acids or amino acids derivatives as for example prolinoamino acids [Mothes C et al., 2008], beta-amino acids [Moumne R et al., 2007], cyclopropylamino acids [Joosten A et al., 2009], N-methylamino acids [Sagan S et al., 2004], and/or alpha-alpha disubstituted amino acids, and/or disubstituted beta-amino acids (Beta2,2, beta3,3 ou beta2,3) and or aza-amino acids (Proulx, C et al., 2011) or azidolysine [Larregola M et al., 2001]. The absolute configurations of the stereogenic centers are not indicated since all the amino acids are natural amino acids or synthetically obtained amino acids, enantiomerically pur from (L) or (D) series or used as racemate.

For model 2, the absolute configurations of the stereogenic centers are not indicated since all the amino acids are natural amino acids or synthetically obtained amino acids, enantiomerically pur from (L) or (D) series or used as racemate.

The R groups (1 to 10) correspond to amino acids side chains that can be natural or synthetic amino acids side chains. For the glycine residue, this side chain correspond to a hydrogen atom.

P1 and P2 correspond to functions respectively on the N-terminal and C-terminal sides of the peptides.

Thus, P1 can be an amine function (P1=—NR11, where R11 is a hydrogen atom or an alkyle chain (similar to methyl, ethyl or benzyl), a carboxylic function (P1=—$CO_2H$), a carboxamide function (P1=—CONR12R13, where R12 and R13 are hydrogen atoms and/or alkyle chains (similar to methyl, ethyl or benzyl) or an amine function, or an azido function ($N_3$).

Thus, P2 can be an amine function (P2=-NR11, where R11 is a hydrogen atom or an alkyle chain (similar to methyl, ethyl or benzyl), a carboxylic function (P2=—$CO_2H$), a carboxamide function (P2=—CONR12R13, where R12 and R13 are hydrogen atoms and/or alkyle chains (similar to methyl, ethyl or benzyl) or an amine function, or an azido function ($N_3$).

Y groups (1 to 10) correspond to hydrogen atoms and/or methyl groups, and/or natural amino acids side chains.

Y1 can also be a protecting group such as an acetamide, a benzamide, a benzyloxycarbonyl, a tertbutyloxycarbonyl, a phenylfluorenylmethoxycarbonyl protecting groups.

Peptides and analogues are synthesized by SPPS or LPPS with Boc, Fmoc or Z strategies. The protonation states of all functions (amino groups, carboxylic functions, guanidinium . . . ) is depending on the syntheses and purifications procedures and can be different from the one indicated on the schemes.

I—Short Analogues Based on Model 1: A1-A2-A3-A4-A5-A6-A7-A8-A9-A10

To improve the solubility and the stability of the octapeptide R-F-Y-V-V-M-W-K (SEQ ID NO:3), the following chemical modifications are realized:

a) Mixed Salts:

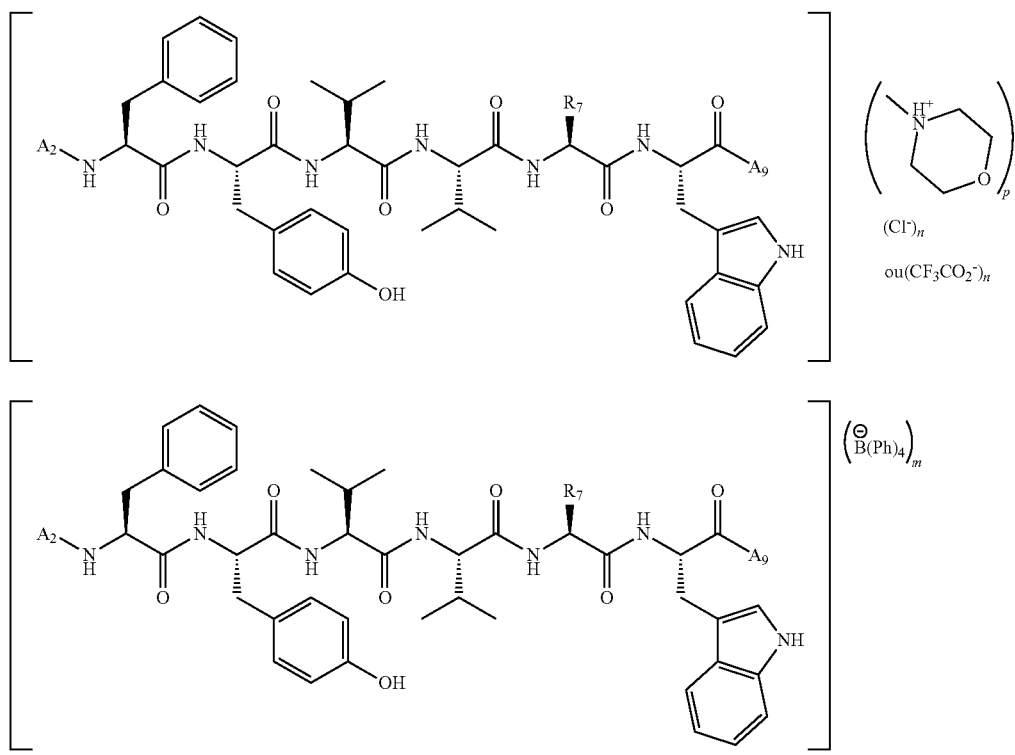

N-methylmorpholine and chlorhydrate or trifluoroacetyl-carboxylate mixed salts:

R7 refers to methionine, methionine sulfoxyde, methionine sulfone or alanine or butylglycine or lysine side chain.

A2 refers to lysine or azidolysine or arginine or bis-ornithine [Aussedat B et al., 2006] or bis-arginine or beta-2-homolysine, or beta-2-homoarginine or beta-2-bis-homoornithine or beta-2-bis-homoarginine. The N-terminal amine function can be free or protected by Boc, Fmoc or Cbz groups, and/or can be N-methylated.

A9 refers to a lysine or arginine or bis-ornithine or bis-arginine or a beta-3-homolysine, or a beta-3-homoarginine or a beta-3-bis-homoornithine or a beta-3-bis-homoarginine. The A9 carboxylic function is free or protected as a carboxamide (P2=—CONR12R13, where R12 and R13 are hydrogen atoms and/or alkyls groups such as methyl, ethyle, benzyl groups and derivatives).

Free or N-methylated amine functions can be obtained as Chlorhydrate or TFA salts (n is variable, depending on the nature of A2, R7 or A9).

Free carboxylic function can be obtained (but not necessarily) as N-methylmorpholine salts (p=1).

PKHB3 is an example of peptide from these series where A2 and A9 correspond respectively to beta-2-homoarginine and beta-3-homolysine:

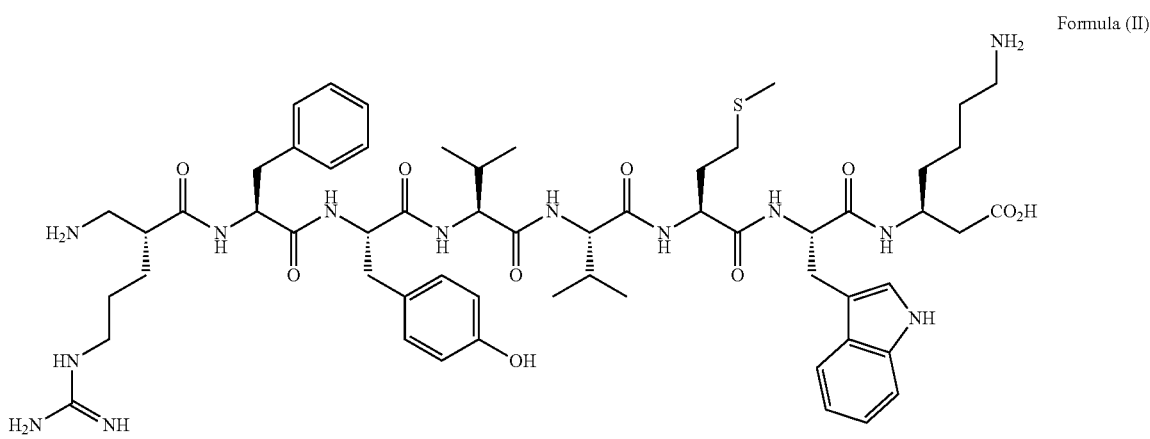

Formula (II)

PKHB3 b) Tetraphenylborate Salts:

R7 corresponds to methionine, methionine sulfoxyde, methionine sulfone or alanine or butylglycine or lysine side chains.

A2 corresponds to lysine or azidolysine or arginine or bis-ornithine or bis-arginine or a beta-2-homolysine, or a beta-2-homoarginine or a beta-2-bis-homoornithine or a beta-2-bis-homoarginine. The free N-terminal amine function can also be protected by a Boc, Fmoc or Cbz groups, and/or N-methylated.

A9 corresponds to lysine or arginine or bis-ornithine or bis-arginine or beta-3-homolysine, or beta-3-homoarginine or beta-3-bis-homoornithine or beta-3-bis-homoarginine. The carboxylic function of A9 is free or protected as a carboxamide (P1=—CONR12R13, where R12 and R13 are hydrogen atoms and/or alkyl groups such as methyl, ethyl, benzyl derivatives).

The free or N-methylated amine functions are obtained as tetraphenylborate salts, m being variable, depending on A2, R7 or A9.

The structure and the syntheses of the peptides below are given as examples:

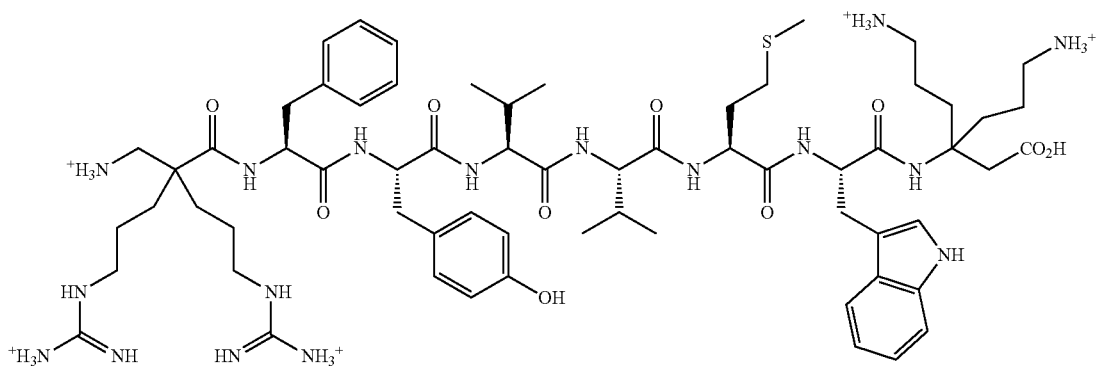

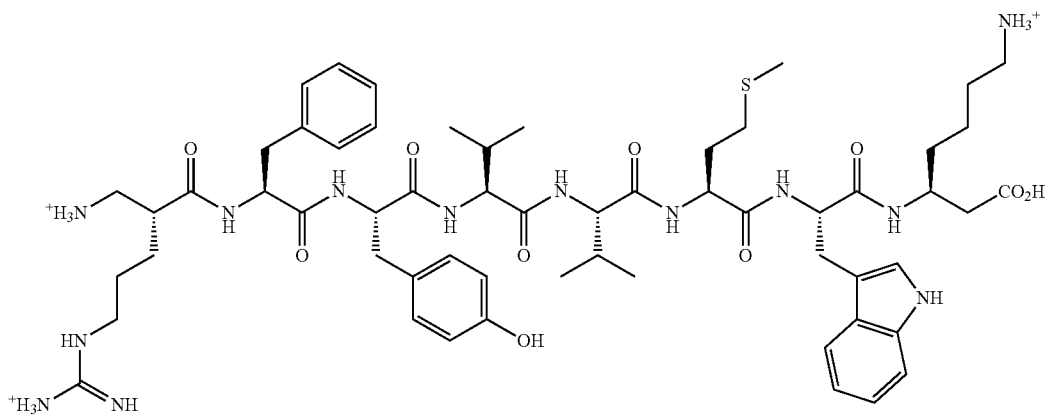

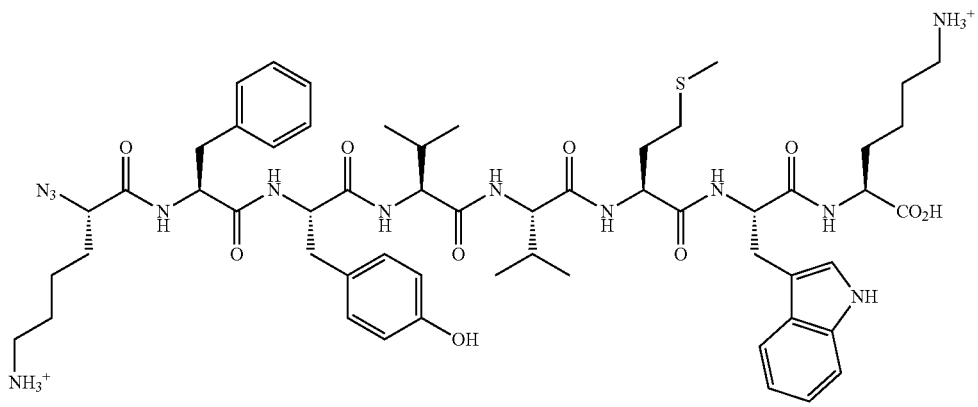

c) N and C-Termini Protections:
The peptides described above are also prepared with N- and C-termini protecting groups.
d) Various Chemical Modifications:
A2-A3-A4-A5-A6-A7-A8-A9        5
N-methyl amino acids are introduced on various positions as described here below:
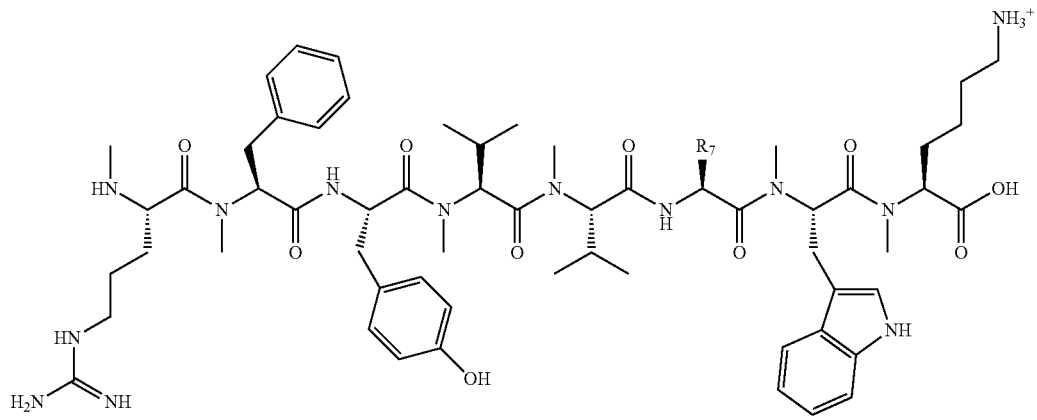
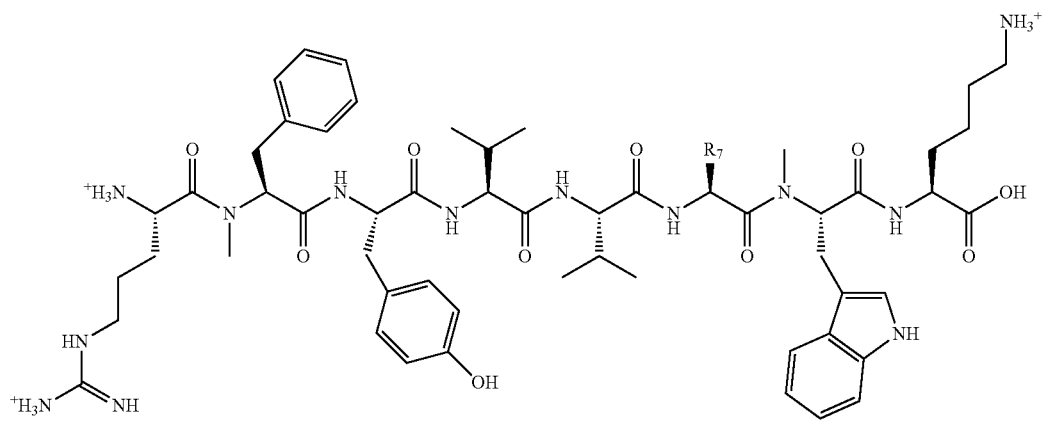
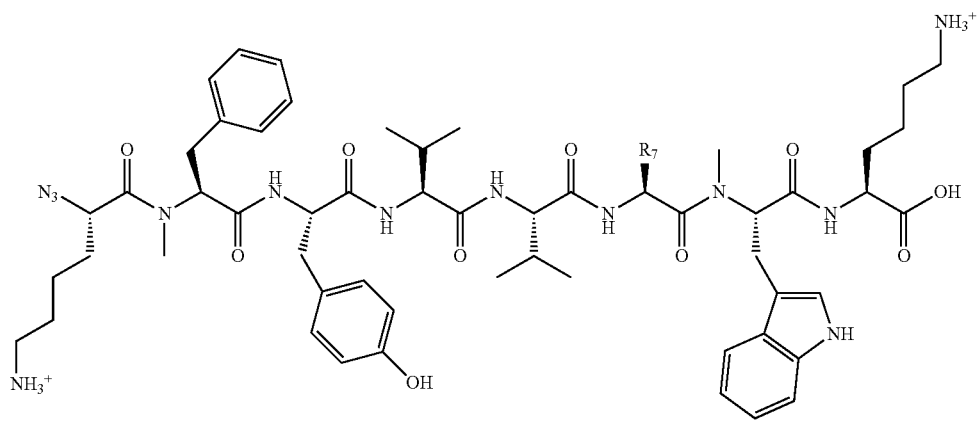
R7 is described above.

e) (D)-Amino Acids:

The introduction of (D)-amino acids in peptide sequences stabilize peptides towards proteolytic degradations and thus enhance its pharmacological properties. (D)-amino acids are introduced on the N terminus and/or on the -terminus and/or instead of one, two, three, four, five, six or seven residues in peptide sequence:

(D)R-F-Y-V-V-M-W-K

R-(D)F-Y-V-V-M-W-K

R-F-(D)Y-V-V-M-W-K

R-F-Y-(D)V-V-M-W-K

R-F-Y-V-(D)V-M-W-K

R-F-Y-V-V-(D)M-W-K

R-F-Y-V-V-M-(D)W-K

R-F-Y-V-V-M-W-(D)K f) Retro-Inverso Sequences:

The retro-inverso sequences led to peptides partially or fully modified with (D)-amino acids keeping however the spatial orientations of crucial amino acids side chains. The following peptides are prepared, incorporating some chemical modifications in order to maintain peptide polarity, around diamine and diacid, introduced respectively on the C-terminus and N-terminus sides:

Inverso Peptides (D)R-(D)F-(D)Y-(D)V-(D)V-(D)M-(D)W-(D)K

Retro-Inverso Peptides (D)K-(D)W-(D)M-(D)V-(D)V-(D)Y-(D)F-(D)R (SEQ ID NO:4)

Azido(D)K-(D)W-(D)M-(D)V-(D)V-(D)Y-(D)F-(D)R

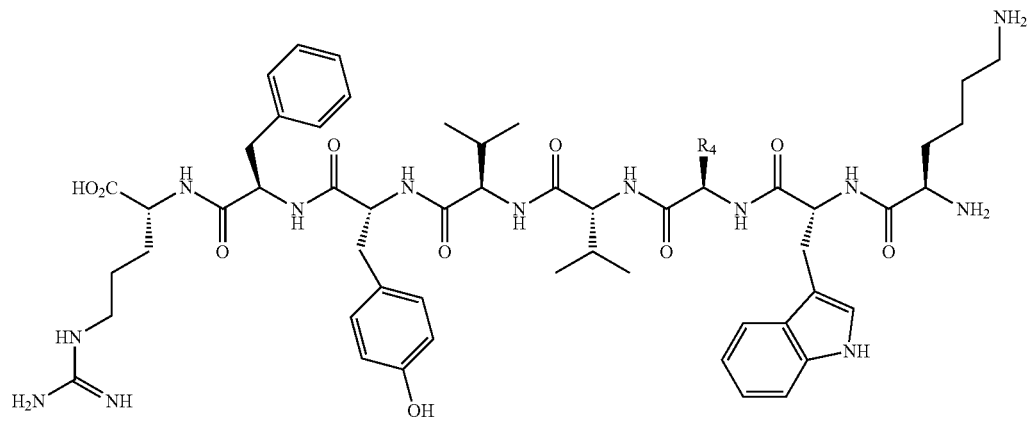

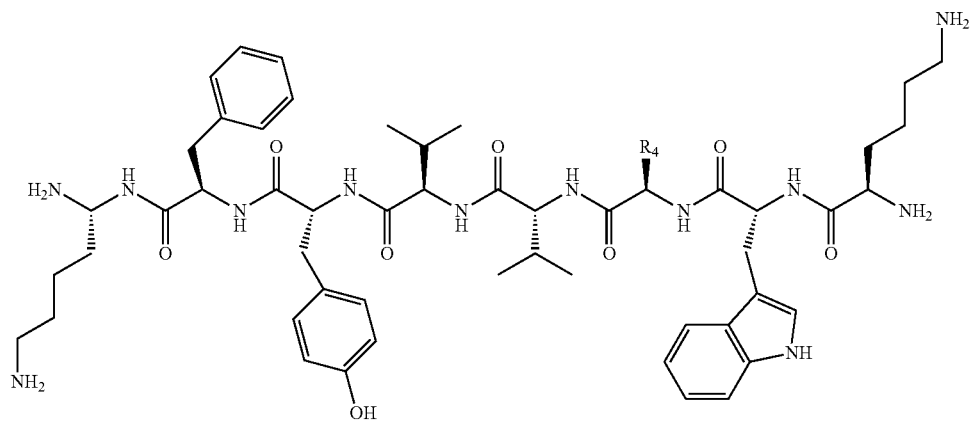

R4 correspond to methionine or alanine or butylglycine or lysine side chains.

g) Some analogues based on model 1: A1-A2-A3-A4-A5-A6-A7-A8-A9-A10 incorporating modified amino acids:

A1 and A10 can correspond to (D)-lysine residues or (D)-arginine residues or beta-2 and/or beta-3 homolysine and/or beta-2 and/or beta-3 homoarginine or beta-2,2 or beta-3,3-homolysine or beta-2,2 or beta-3,3homoarginine. PKHB4 (formula III) is an example from this series where A10 have been replaced by a (D)-Lysine residue:

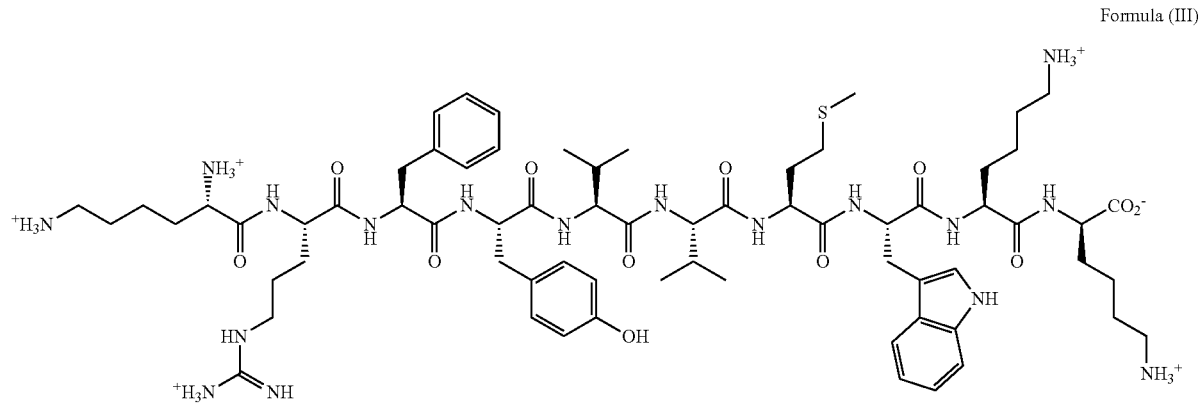

Formula (III)

PKHB11 is another example of peptide from this series where both A1 and A2 residues have been replaced by the beta-2,2 homolysine and a D-lysine has been introduced in C-terminal position of the peptide (see for example PKHB11 (formula (IV))):

Formula (IV)

PKHB11

A2 can correspond to arginine or lysine residues.

N-methylated amino acids or cyclopropylamino acids can be introduced in the sequence in position A2 and/or A3 and/or A4 and/or A5 and/or A6 and/or A7 and/or A8 and/or A9. A prolinovaline can be introduced in position A5 and/or A6. PKHB9 (formula (V)) and PKHB10 (formula (VI)) are both example of peptide from this series:

Formula (V)

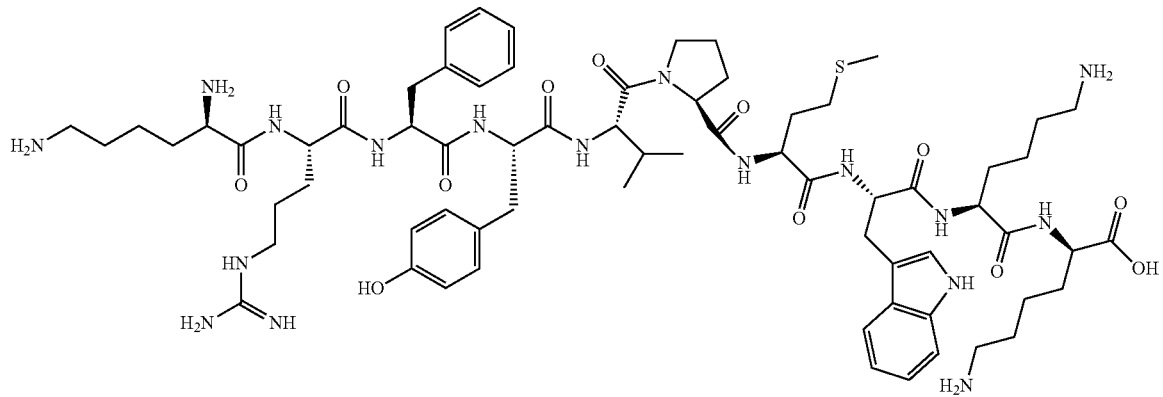

PKHB9

Formula (VI)

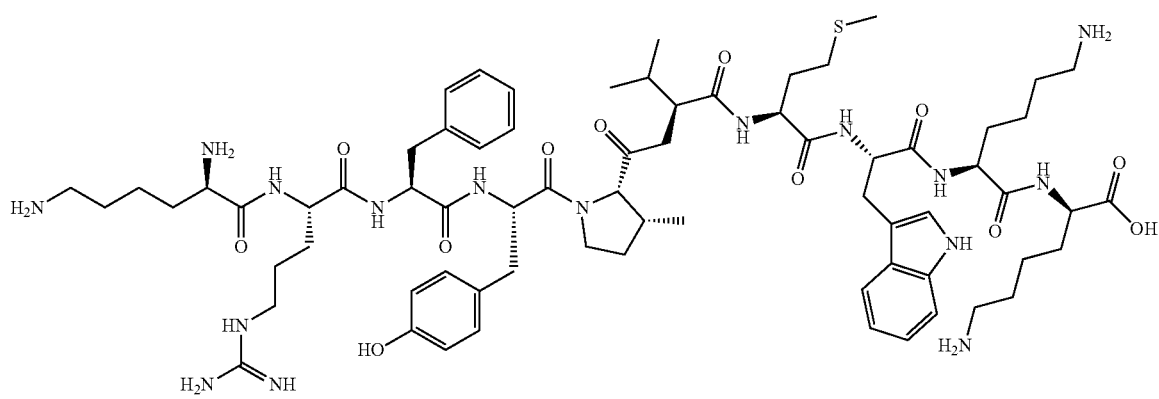

PKHB10

A prolinomethionine can be introduced in position A7.
A prolinotryptophane or prolinohomotryptophane can be introduced in position A8.
A prolinolysine can be introduced in position A9.

II—Analogues Based on Model 2:

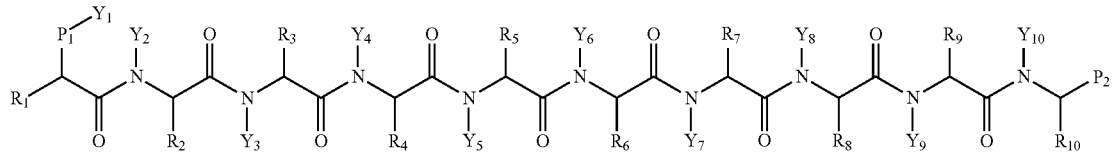

a) Protections of N- and C-Termini of the Peptide

P1 is an amine function (P1═NR11, where R11 is a hydrogen atom or an alkyl chain such as a methyl group for example) or a carboxylic acid (P1═—CO$_2$H) or an azido group (N$_3$).

P2 can be an amine function (P2═NR11, where R11 is a hydrogen atom or an alkyl chain such as a methyl group for example) or a carboxylic acid (P1═—CO$_2$H) or an azido group (N$_3$).

The following peptide is given as an example:

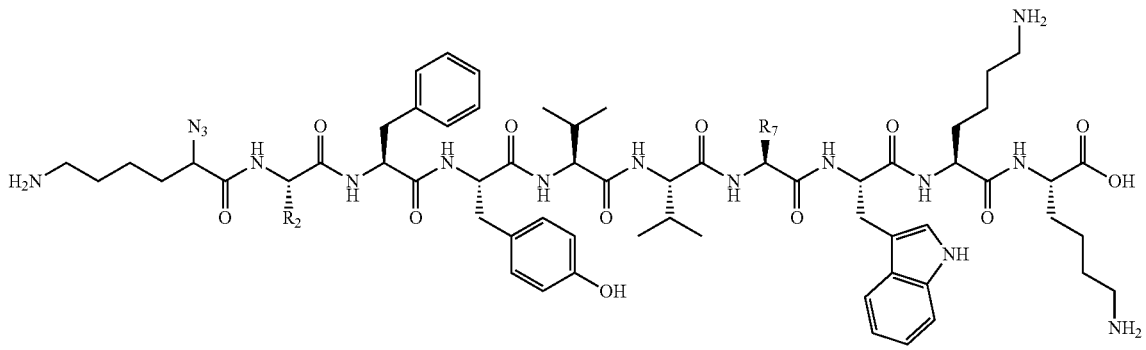

An azido group is present on the N-terminal side. An azido-lysine with S or R configuration is introduced. The R2 group corresponds to lysine or arginine side chains. R7 group corresponds to methionine side chain, methionine sulfoxyde side chain, methionine sulfone side chain or a methyl, or an n-butyl or lysine side chain.

b) Amino Acids Sequence Modifications
(D) Residues:

K-R-F-Y-V-V-M-(D)W-K-K

R-R-F-Y-V-V-M-W-(D)K-K

K-R-F-Y-V-V-M-W-K-(D)K

K-R-F-Y-V-V-M-W-K-(D)R (D)K-R-F-Y-V-V-M-W-K-(D) (=peptide PKHB1, formula (I))

Formula (I)

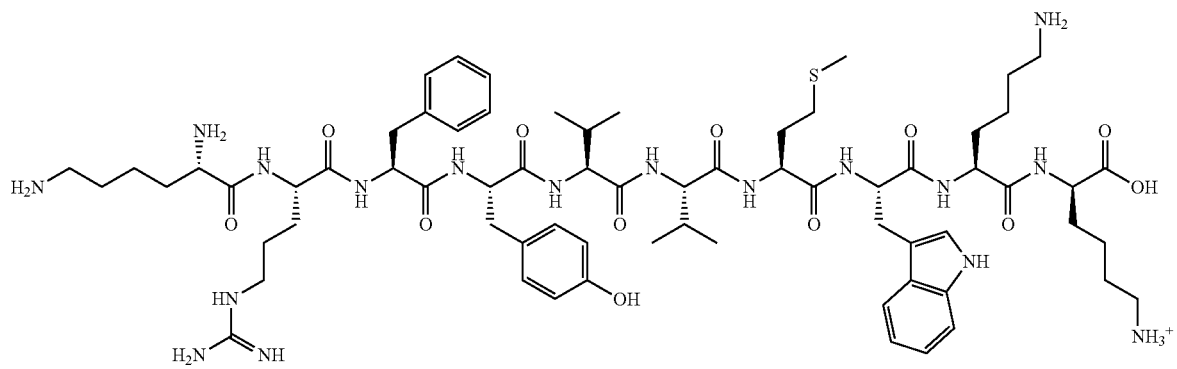

PKHB1

The introduction of (D)-amino acids in peptide sequences stabilize peptides towards proteolytic degradations and thus enhance its pharmacological properties. (D)-amino acids are introduced on the N terminus and/or on the C-terminus and/or instead of one, two, three, four, five, six, seven, eight or nine residues in peptide sequence:

(D)K-R-F-Y-V-V-M-W-K-K

K-(D)R-F-Y-V-V-M-W-K-K

K-R-(D)F-Y-V-V-M-W-K-K

K-R-F-(D)Y-V-V-M-W-K-K

K-R-F-Y-(D)V-V-M-W-K-K

K-R-F-Y-V-(D)V-M-W-K-K

K-R-F-Y-V-V-(D)M-W-K-K

The retro-inverso sequences lead to peptides partially or fully modified with (D)-amino acids keeping however the spatial orientations of crucial amino acids side chains. The following peptides are prepared, incorporating some chemical modifications in order to maintain peptide polarity, around diamine and diacid, introduced respectively on the C-terminus and N-terminus sides:

Inverso Peptide (D)K-(D)R-(D)F-(D)Y-(D)V-(D)V-(D)M-(D)W-(D)K-(D)K

Retro-Inverso Peptide (D)K-(D)K-(D)W-(D)M-(D)V-(D)V-(D)Y-(D)F-(D)R-(D)K (SEQ ID NO:5)

Specific chemical modifications are introduced in retro-inverso peptide sequence in order to keep peptide polarity. The following peptides are prepared:

Retro-Inverso Modified Peptide

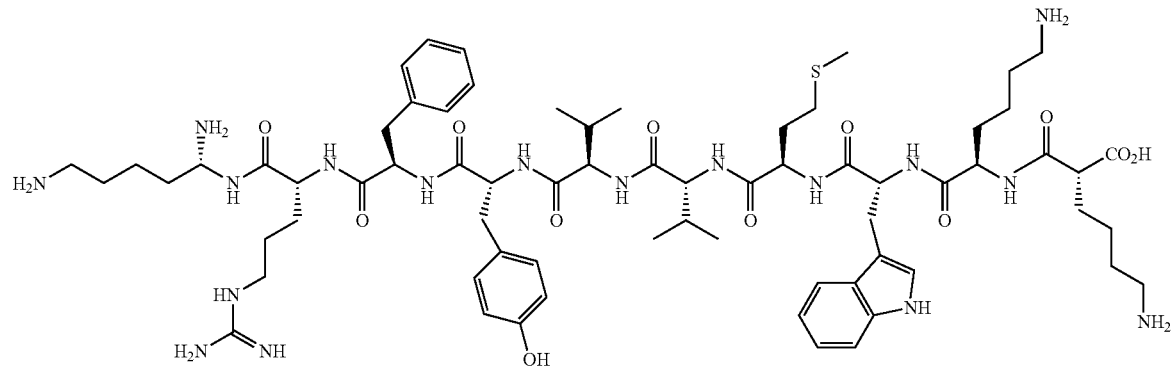

In this peptide, (D)-amino acids are introduced instead of (L)-amino acids, excepted on the N-terminus and C-terminus where diacide (N-terminus) and diamine (C-terminus) are introduced keeping 4N1K peptide polarity.

III—Polymer Analogues

Polymers (dimers or trimers) analogues are obtained by reacting the azidopeptides (short or long analogues) through Huisgen type cycloaddition reactions:

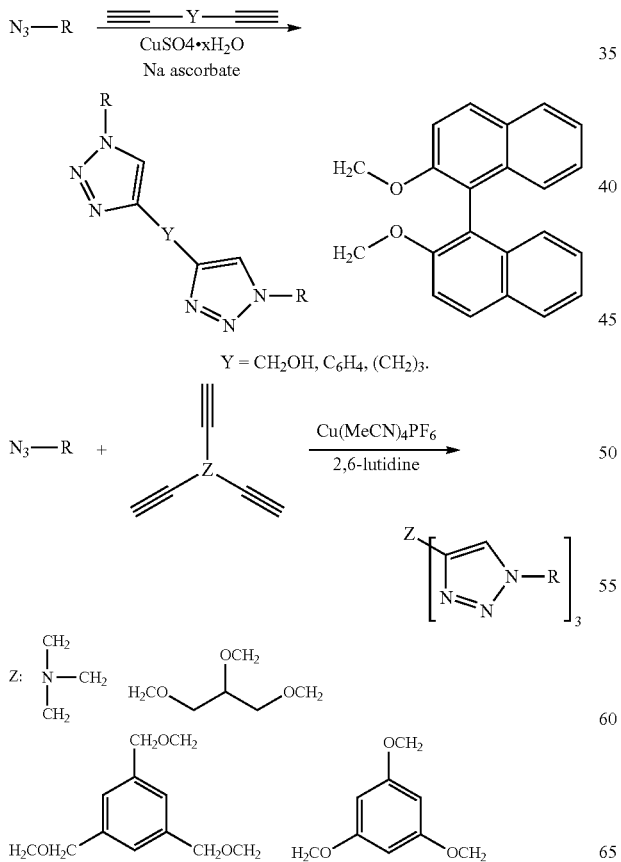

For example, trimer analogues are obtained by reacting the azidopeptides (short or long analogues) with tripropargylamine as followed:

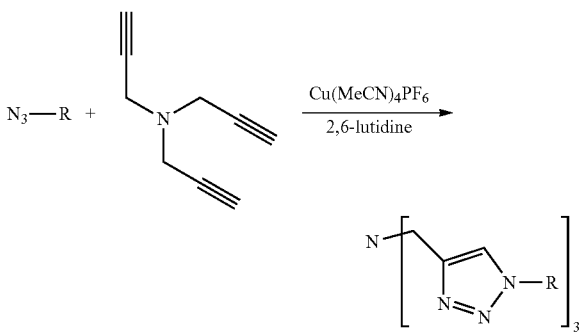

The R group corresponds to sequences of azidopeptides described here above.

V—Test of Generated Soluble Peptides

1.—To verify whether the newly generated soluble peptides induce the same type of caspase-independent PCD than the initially characterized peptide 4N1K, a flow cytometry analysis (such as described in FIG. 2) is performed with each peptide. A comparison of the results obtained in treatments with/without the caspase inhibitor Z-VAD.fmk corroborate that the mode of cell death induced by the 4N1K-derived peptides is caspase-independent. Additionally, a time-course and a dose-response performed in different tumor cells determine the optimal conditions for each peptide and each malignant cell type.

2.—As shown in FIGS. 3 and 4 the induction of 4N1K induces a potent and sustained increase of calcium mobilization. This $Ca^{2+}$ overload dramatically changes the morphological structure of organelles such as mitochondria driving cells in apoptosis. Therefore, using our ion measurement platform, we assess $Ca^{2+}$-mobilization in fura-2 loaded CLL cells triggered by the 4N1K-derived peptides.

3.—Since we have shown that the injection of the 4N1K derivatives such as PKHB1 peptide may be used to eliminate B leukemia cells in vivo (FIG. 7), we use the same approach and test the newly synthesized and in vitro-validated peptides. The objective is to corroborate whether the peptides generated are efficient in inducing tumor regression in vivo. To do so, the CLL established MEC1 B-cells are injected subcutaneously into the flanks of NSG (NOD scid gamma) mice, one of the most suitable immunodeficient strain. The mice with established lymphoma are treated 3 times a week for 4 weeks by intraperitoneal injections of the 4N1K derivatives or PBS control, and the development of the tumor is followed by caliper measurement and by a non-invasive optical analysis performed in a Kodak in vivo-imaging system FX-Pro using the 2-DG-750 probe (Tumor volume is monitored every other day).

Example 3

Use of PKHB1 as Therapeutic Compound

The PKHB1 compound correspond to the peptide 4N1K (SEQ ID NO:1) with amino acids C-terminal and N-Terminal (A1 and A10 of SEQ ID NO:1) in (D)-amino acids (dextrorotary amino acids) version as explained in example 2 part II b)).

The PKHB1 peptide is not degradated in human serum experiments and has proven to be stable over 6 hours (FIG. 8).

The PKHB1 peptide shows clearly a better efficiency than the 4N1K peptide on B cells isolated from CLL patients (FIG. 6A). This was verified in a cohort of 14 CLL patients with diverse prognostic features, including unmutated IGHV, complex karyotype and dysfunctional TP53 (FIG. 6B, 4N1K induced about 45% of cell death in CLL cells at 300 µM, whereas PKHB1 induced a similar rate of death at 150 µM). Moreover, as 4N1K, PKHB1 induced cytotoxicity in malignant cells but not in normal B-lymphocytes (FIG. 6C, PKHB1 significantly killed the CD19$^+$/CD5$^+$ tumor cells, but the residual CD19$^+$/CD5$^-$ B-lymphocytes were resistant to this peptide, n=8). Finally, we have corroborated that pre-treatment of CLL cells with BAPTA-AM, an intra-cellular Ca$^{2+}$ chelator, significantly decreased PKHB1-mediated PCD in CLL cells (FIG. 6D, n=10). These results confirmed that PKHB1 induced cell death in CLL in a similar way than 4N1K, via an intracellular calcium mobilization. Overall, our results on PKHB1 confirmed that the introduction of (D)-amino acids in the peptide sequence of 4N1K enhanced its pharmacological cell death activity.

Since the PKHB1 had a better stability and in vitro effect, we tested the in vivo role of PKHB1 in tumor growth. As depicted in FIG. 7, only few days after PKHB1 injection, we observed a reduction of both the tumor growth and glucose uptake compared to control mice. These in vivo results emphasize the use of the 4N1K derivatives, like PKBH1, as therapeutic tools for the eradication of tumor cells.

REFERENCES

Throughout this application, various references describe the state of the art to which this invention pertains. The disclosures of these references are hereby incorporated by reference into the present disclosure.

Aussedat B., G. Chassaing, S. Lavielle, F. Burlina. Bis-ornithine (2,2-bis(aminopropyl)glycine): a new tetravalent template for assembling different functional peptides. Tetrahedron Lett. 2006, 47, 3723-3726.

Barbier S, Chatre L, Bras M, Sancho P, Roue G, Virely C et al. Caspase-independent type III programmed cell death in chronic lymphocytic leukemia: the key role of the F-actin cytoskeleton. Haematologica 2009; 94(4): 507-17.

Bras M, Yuste V J, Roue G, Barbier S, Sancho P, Virely C et al. Drp1 Mediates Caspase-Independent Type III Cell Death in Normal and Leukemic Cells. Mol Cell Biol 2007; 27(20): 7073-88.

Brown E J, Frazier W A. Integrin-associated protein (CD47) and its ligands. Trends Cell Biol 2001; 11(3): 130-5.

Chao, M. P., Alizadeh, A. A., Tang, C., Myklebust, J. H., Varghese, B., Gill, S., Jan, M., Cha, A. C., Chan, C. K., Tan, B. T., et al. 2010. Anti-CD47 antibody synergizes with rituximab to promote phagocytosis and eradicate non-Hodgkin lymphoma. Cell 142:699-713.

Chao, M. P., Alizadeh, A. A., Tang, C., Jan, M., Weissman-Tsukamoto, R., Zhao, F., Park, C. Y., Weissman, I. L., and Majeti, R. 2011. Therapeutic antibody targeting of CD47 eliminates human acute lymphoblastic leukemia. Cancer Res 71:1374-1384.

Chiorazzi N. Cell proliferation and death: forgotten features of chronic lymphocytic leukemia B cells. Best practice & research 2007; 20(3): 399-413.

Chiorazzi N, Rai K R, Ferrarini M. Chronic lymphocytic leukemia. N Engl J Med 2005; 352(8): 804-15.

Edris, B., Weiskopf, K., Volkmer, A. K., Volkmer, J. P., Willingham, S. B., Contreras-Trujillo, H., Liu, J., Majeti, R., West, R. B., Fletcher, J. A., et al. 2012. Antibody therapy targeting the CD47 protein is effective in a model of aggressive metastatic leiomyosarcoma. Proc Natl Acad Sci USA 109:6656-61.

Gribben J G. How I treat CLL up front. Blood 2010; 115(2): 187-97.

Jaiswal, S., Jamieson, C. H., Pang, W. W., Park, C. Y., Chao, M. P., Majeti, R., Traver, D., van Rooijen, N., and Weissman, I. L. 2009. CD47 is upregulated on circulating hematopoietic stem cells and leukemia cells to avoid phagocytosis. Cell 138:271-285.

Lanasa M C. Novel insights into the biology of CLL. Hematology Am Soc Hematol Educ Program 2010; 2010: 70-6.

Joosten, A.; Pradhan, T. K.; Vasse, J-L.; Bertus, P.; Karoyan, P.; Szymoniak, J. A Concise Stereoselective Synthesis of 2-Substituted 1-Aminocyclopropanecarboxylic Acids. 2009. 29, 5072-5078.

Larregola, M; Lequin, Olivier; Karoyan, Philippe; Guianvarc'h, Dominique; Lavielle, Solange. β-Amino acids containing peptides and click-cyclized peptide as β-turn mimics: a comparative study with "conventional" lactam- and disulfide-bridged hexapeptides. Journal of Peptide Science (2011), 17(9), 632-643.

Lukaszuk A, Demaegdt H, Szemenyei E, Toth G, Tymecka D, Misicka A, Karoyan P, Vanderheyden P, Vauquelin G, Tourwé D. J. Beta-homo-amino acid scan of angiotensin IV. Med Chem. 2008 Apr. 10; 51(7) 2291-6.

Mateo V, Lagneaux L, Bron D, Biron G, Armant M, Delespesse G et al. CD47 ligation induces caspase-independent cell death in chronic lymphocytic leukemia. Nat Med 1999; 5(11): 1277-84.

Mateo V, Brown E J, Biron G, Rubio M, Fischer A, Deist F L et al. Mechanisms of CD47-induced caspase-independent cell death in normal and leukemic cells: link between phosphatidylserine exposure and cytoskeleton organization. Blood 2002; 100(8): 2882-90.

Merle-Beral H, Barbier S, Roue G, Bras M, Sarfati M, Susin S A. Caspase-independent type III PCD: a new means to modulate cell death in chronic lymphocytic leukemia. Leukemia 2009; 23(5): 974-7.

Moumne, R.; Denise, B.; Guitot, K.; Rudler, H.; Lavielle, S.; Karoyan, P. New scalable asymmetric aminomethylation reaction for the synthesis of β 2-amino acids. Eur. J. Org. Chem., 2007, 1912-1920.

Mothes, C. Lavielle, S.; Karoyan, Ph. J. Amino-Zinc-Ene-Enolate Cyclization: A short access to cis-3-substituted Prolino-homotryptophane Derivatives. Org. Chem., 2008, 73(17); 6706-6710.

Pospisilova S, Gonzalez D, Malcikova J, Trbusek M, Rossi D, Kater A P et al. ERIC recommendations on TP53 mutation analysis in chronic lymphocytic leukemia. Leukemia 2012.

Proulx, Caroline; Sabatino, David; Hopewell, Robert; Spiegel, Jochen; Garciia Ramos, Yeesica; Lubell, William D. Azapeptides and their therapeutic potential. From Future Medicinal Chemistry (2011), 3(9), 1139-1164.

Roue G, Bitton N, Yuste V J, Montange T, Rubio M, Dessauge F et al. Mitochondrial dysfunction in CD47-mediated caspase-independent cell death: ROS production in the absence of cytochrome c and AIF release. Biochimie 2003; 85(8): 741-6.

Sagan S; Philippe Karoyan; Olivier Lequin; Gerard Chassaing; Solange Lavielle. N- and Cα-Methylation in Biologically Active Peptides: Synthesis, Structural and Functional Aspects. Current Medicinal Chemistry, Volume 11, Number 21, November 2004, pp. 2799-2822(24).

Willingham, S. B., Volkmer, J. P., Gentles, A. J., Sahoo, D., Dalerba, P., Mitra, S. S., Wang, J., Contreras-Trujillo, H., Martin, R., Cohen, J. D., et al. 2012. The CD47-signal regulatory protein alpha (SIRPa) interaction is a therapeutic target for human solid tumors. Proc Natl Acad Sci USA 109:6662-6667.

The invention claimed is:
1. A method for treating cancer in an individual comprising administering to the individual a therapeutically effective amount of a peptide of the following formula (I), or a pharmaceutically acceptable salt thereof:

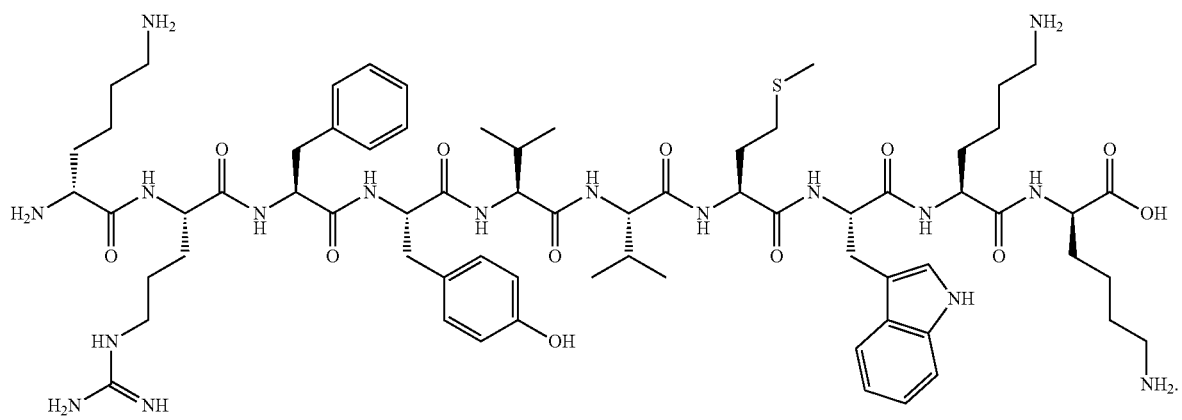

PKHB1 wherein the cancer is leukemia, breast cancer, colorectal cancer, pancreatic cancer or glioblastoma.

2. The method of claim 1, wherein the cancer is acute lymphoblastic leukemia, B-chronic lymphocytic leukemia, hairy-cell leukemia, adult T-cell leukemia, prolymphocytic leukemia of T-cell type or myeloid leukemia.

3. The method of claim 1, wherein the cancer is B-chronic lymphocyte leukemia (CCL).

4. The method of claim 1, wherein the cancer is refractory chronic lymphocyte leukemia (CCL).

5. A method of destructing tumor cells, comprising contacting the tumor cells with an effective amount of a peptide of the following formula (I), or a pharmaceutically acceptable salt thereof:

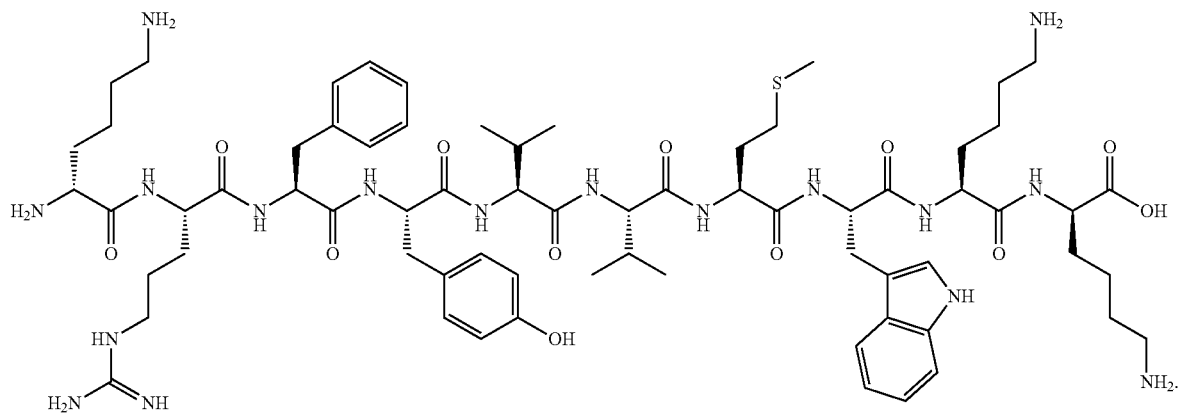

PKHB1

6. A peptide of the following formula (I):

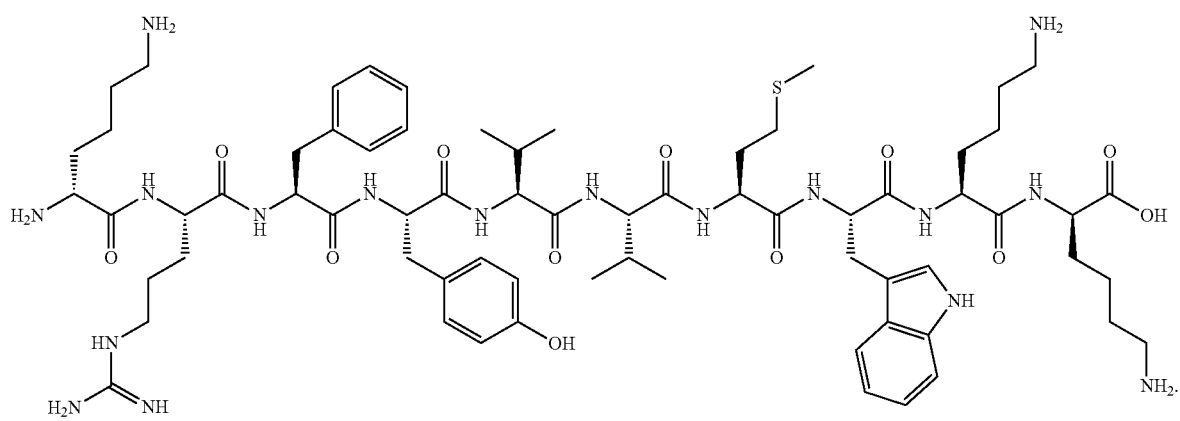

PKHB1

7. A pharmaceutical composition comprising the peptide of claim 6, or a pharmaceutical acceptable salt thereof, and at least one pharmaceutically acceptable carrier.

8. The pharmaceutical composition of claim 7, which is formulated for a topical, oral, intranasal, intraocular, intravenous, intramuscular or subcutaneous administration.

9. The pharmaceutical composition of claim 7, which is in an injectable form.

* * * * *